(12) United States Patent
Aburatani et al.

(10) Patent No.: US 10,563,265 B2
(45) Date of Patent: Feb. 18, 2020

(54) USE OF RHOA IN CANCER DIAGNOSIS AND INHIBITOR SCREENING

(71) Applicants: The University of Tokyo, Tokyo (JP); Chugai Seiyaku Kabushiki Kaisha, Tokyo (JP)

(72) Inventors: Hiroyuki Aburatani, Tokyo (JP); Shumpei Ishikawa, Tokyo (JP); Miwako Kakiuchi, Tokyo (JP); Takashi Nishizawa, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 14 days.

(21) Appl. No.: 14/916,442

(22) PCT Filed: Sep. 4, 2014

(86) PCT No.: PCT/JP2014/004539
§ 371 (c)(1),
(2) Date: Mar. 3, 2016

(87) PCT Pub. No.: WO2015/033565
PCT Pub. Date: Mar. 12, 2015

(65) Prior Publication Data
US 2016/0208335 A1 Jul. 21, 2016

(30) Foreign Application Priority Data
Sep. 6, 2013 (JP) .................. 2013-185493

(51) Int. Cl.
C12Q 1/6886 (2018.01)
C12N 9/14 (2006.01)
C12N 15/113 (2010.01)

(52) U.S. Cl.
CPC ............. *C12Q 1/6886* (2013.01); *C12N 9/14* (2013.01); *C12N 15/1137* (2013.01); *C12N 2310/14* (2013.01); *C12N 2320/30* (2013.01); *C12Q 2600/136* (2013.01); *C12Q 2600/156* (2013.01); *C12Q 2600/158* (2013.01); *C12Q 2600/178* (2013.01); *C12Y 306/05002* (2013.01)

(58) Field of Classification Search
CPC ........ G01N 33/5011; G01N 33/57415; G01N 33/57419; G01N 33/57423; G01N 33/57446
See application file for complete search history.

(56) References Cited

U.S. PATENT DOCUMENTS

| 9,446,062 B2 * | 9/2016 | Feinstein | ................ A61K 31/70 |
| 2001/0044414 A1 | 11/2001 | Clark et al. | |
| 2009/0162365 A1 * | 6/2009 | Feinstein | ................ A61K 31/70 424/139.1 |
| 2010/0003257 A1 | 1/2010 | Juang et al. | |
| 2016/0076107 A1 * | 3/2016 | Chiba | ................... C12Q 1/6886 506/9 |

FOREIGN PATENT DOCUMENTS

| JP | 2012-511031 | | 5/2012 | |
| WO | WO 2003/030836 A2 | | 4/2003 | |
| WO | WO-2005113770 A1 | | 12/2005 | |
| WO | WO2008/050329 | * | 5/2008 | |
| WO | WO 2010/065961 A2 | | 6/2010 | |
| WO | WO 2011/163436 A1 | | 12/2011 | |
| WO | WO-2014178432 A1 | * | 11/2014 | ........... C12Q 1/6886 |
| WO | WO 2014/197453 A1 | | 12/2014 | |

OTHER PUBLICATIONS

Robinson, PLoS Biology, 2004, vol. 2, No. 1, pp. 0018-0020.*
Zhang et al (Journal of Controlled Release, 2013, vol. 172, pp. 962-974).*
Bae et al (Journal of Biological Chemistry, 1998, vol. 273, pp. 11596-11604).*
Sahai et al (The EMBO Journal, 1998, vol. 17, pp. 1350-1361).*
Sakata-Yanagimoto et al (Nature Genetics, Jun. 2014, vol. 46, pp. 171-178).*
Kakiuchi et al, supplemental Table 6 (from Nature Genetics, Jun. 2014, vol. 46, pp. 583-587).*
Watts et al, Drug Discovery Today, 2008, vol. 13, pp. 842-855.*
Life Technologies Product Insert PN 4457171, Aug. 2011).*
Molina-Privado et al (Leukemia, 2012, vol. 26, pp. 2277-2285).*
Campbell (Monoclonal Antibody Technology, 1984, pp. 1-32).*
TableB49 associated with U.S. Pat. No. 9,446,062/U.S.2009/0162365, downloaded from the Web on Oct. 18, 2018. (Year: 2018).*
Guggenheim, D. E., et al., "Gastric Cancer Epidemiology and Risk Factors," *Journal of Surgical Oncology*; 107: 230-236 (2013).
Jemal, A., et al., "Global Cancer Statistics," *CA Cancer J. Clin.*; 61(2): 69-90 (2011).
NCCN Clinical Practice Guidelines in Oncology (NCCN Guidelines®), "Gastric Cancer," Version 3.2015; *National Comprehensive Cancer Network, Inc.* (2015).
Bang, Y. J., et al., "Trastuzumab in combination with chemotherapy versus chemotherapy alone for treatment of HER2-positive advanced gastric or gastro-oesophageal junction cancer (ToGA): a phase 3, open-label, randomised controlled trial," *Lancet*; 376: 687-697 (Aug. 28, 2010).
Nishikawa, K., et al., 2013 Gastrointestinal Cancers Symposium, "Result of HER2 status in Japanese metastatic gastric cancer: Prospective cohort study (JFMC44-1101)," *J. Clin. Oncol.* 31 (suppl 4; abstr 10) (2013).

(Continued)

*Primary Examiner* — Karen A. Canella
(74) *Attorney, Agent, or Firm* — Nixon & Vanderhye P.C.

(57) ABSTRACT

Disclosed are a novel method of detecting cancer, a method of screening inhibitors and anticancer agents that target cancer-related molecules, RHOA polypeptide having mutation and a polynucleotide encoding the polypeptide as a therapeutic agent for cancer, and a method of detecting cancer using the polypeptide or polynucleotide. Also disclosed are a vector and a host cell comprising the polynucleotide, a method of screening therapeutic agents for cancer comprising the polypeptide and/or the polynucleotide, and a therapeutic agent for cancer comprising siRNA having a silencing effect on RHOA mutant.

12 Claims, 9 Drawing Sheets
Specification includes a Sequence Listing.

(56) References Cited

OTHER PUBLICATIONS

Ohtsu, A., et al., "Bevacizumab in Combination With Chemotherapy As First-Line Therapy in Advanced Gastric Cancer: A Randomized, Double-Blind, Placebo-Controlled Phase III Study," *J. Clin. Oncol.*; 29(30): 3968-3976 (Oct. 20, 2011).

Lordick, F., et al., "Capecitabine and cisplatin with or without cetuximab for patients with previously untreated advanced gastric cancer (EXPAND): a randomised, open-label phase 3 trial," *Lancet Oncol.*; 14: 490-499 (May 2013).

Sahai, E., et al., "RHO-GTPases and Cancer," *Nature Reviews Cancer*; 2: 133-142 (Feb. 2002).

Karlsson, R., et al., "RHO GTPase function in tumorigenesis," *Biochimica et Biophysica Acta*; 1796: 91-98 (2009).

Grise, F., et al., "Rho GTPases in hepatocellular carcinoma," *Biochimica et Biophysica Acta*; 1795: 137-151 (2009).

Chan, C. H., et al., "Deciphering the transcriptional complex critical for RhoA gene expression and cancer metastasis," *Nature Cell Biology*; 12(5): 457-467 (May 2010).

Waheed, F., et al., "Affinity Precipitation of Active Rho-GEFs Using a GST-tagged Mutant Rho Protein (GST-RhoA(G17A)) from Epithelial Cell Lysates," *Journal of Visualized Experiments*; 61(e3932): 1-5 (Mar. 2012).

Longenecker, K., et al., "Structure of a constitutively activated RhoA mutant (Q63L) at 1.55 Å resolution," *Acta Crystallographica Section D: Biological Crystallography*; D59: 876-880 (2003).

Palomero, T., et al., "Recurrent mutations in epigenetic regulators, RHOA and FYN kinase in peripheral T cell lymphomas," *Nature Genetics*; 46(2): 166-170 (Feb. 2014).

Wang, K., et al., "Whole-genome sequencing and comprehensive molecular profiling identify new driver mutations in gastric cancer," *Nature Genetics*; 46(6): 573-582 (Jun. 2014).

Yoo, H. Y., et al., "A recurrent inactivating mutation in RHOA GTPase in angioimmunoblastic T cell lymphoma," *Nature Genetics*; 46(4): 371-375 (Apr. 2014).

Sakata-Yanagimoto, M., et al., "Somatic RHOA mutation in angioimmunoblastic T cell lymphoma," *Nature Genetics*; 46(2): 171-175 (Feb. 2014).

Chiba, S., et al., "G17V RHOA: Genetic evidence of GTP-unbound RHOA playing a role in tumorigenesis in T cells," *Small GTPases*; 6(2): 100-103 (2015).

Ondrejka, S. L., et al., "Angioimmunoblastic T-cell Lymphomas With the RHOA p.Gly17Val Mutation Have Classic Clinical and Pathologic Features," *Am. J. Surg. Pathol.*; 00(00): 1-7 (2015).

The Cancer Genome Atlas Research Network, "Comprehensive molecular characterization of gastric adenocarcinoma," *Nature*; 513: 202-209 (Sep. 11, 2014).

Ushiku, T., et al., "RHOA mutation in diffuse-type gastric cancer: a comparative clinicopathology analysis of 87 cases," *Gastric Cancer*; published online: Apr. 1, 2015.

Kakiuchi, M, et al., "Recurrent gain-of-function mutations of RHOA in diffuse-type gastric carcinoma," *Nature Genetics*; 46(6): 583-587 (Jun. 2014).

Rodrigues, P., et al., "RHOA inactivation enhances Wnt signaling and promotes colorectal cancer," *Nature Communications*; 5(5458) DOI: 10.1038/ncomms6458: 1-15 (Nov. 21, 2014).

International Search Report, dated Dec. 9, 2014, issued in connection with corresponding International Application No. PCT/JP2014/004539.

Verified Translation of document JP 2013-185493, filed on Sep. 6, 2013, dated Mar. 21, 2017.

Richter, J., et al., "Recurrent Mutation of the ID3 Gene in Burkitt Lymphoma Identified by Integrated Genome, Exome and Transcriptome Sequencing," Nature Genetics 44(12):1316-1320, Nature America, Inc., United States (2012).

Partial Supplementary European Search Report for EP Application No. 14841672.0, European Patent Office, Munich, Germany, dated Mar. 27, 2017, 8 pages.

\* cited by examiner

USE OF RHOA IN CANCER DIAGNOSIS AND INHIBITOR SCREENING

TECHNICAL FIELD

The present invention relates to a RHOA polypeptide comprising mutation(s), a polynucleotide encoding the polypeptide, a vector and a host cell comprising the polynucleotide. The present invention also relates to a method of screening therapeutic agents for cancer comprising the polypeptide and/or the polynucleotide, a method of detecting the cancer, and a therapeutic agent for cancer to be administered to a subject with the cancer.

BACKGROUND

Gastric cancer is the 4th most common cancer in men worldwide, following lung cancer, prostate cancer, and colorectal cancer and is the 5th most common cancer in women (Non Patent Literature 1). Gastric cancer killed an estimated 464,000 men and an estimated 273,000 women in 2011 (Non Patent Literature 2). There is thus a significant medical need. Gastric cancer is very common in some regions including East Asia, Middle Eastern Europe, and South America and is the highest incidence cancer in men in Japan (Non Patent Literature 3).

Trastuzumab, which is a molecular target drug, was approved by FDA in 2010 based on the clinical trial results for patients with HER2-positive gastric cancer (Non Patent Literature 4). However, the HER2-positive rate was reported to be about 30% in the intestinal type gastric cancer and 10% or lower in the diffuse type gastric cancer (Non Patent Literature 5). Therefore, there is still a significant medical need to treat patients with gastric cancer. VEGF and EGFR are molecules known to be highly expressed in gastric cancer. Bevacizumab, which is an anti-VEGF antibody drug, and Cetuximab, which is an anti-EGFR antibody drug, proceeded to phase 3 clinical trials but both failed to be approved due to insufficient drug efficacy (Non Patent Literatures 6 and 7). This requires development of new drugs.

RHOA, which is a molecule belonging to the RAS small GTPase super family, is known to be highly expressed in cancer sites in a wide variety of cancer types, including breast cancer, colorectal cancer, liver cancer, esophageal cancer, gastric cancer, and lung cancer, at mRNA and protein levels (Non Patent Literatures 8-10). The high expression of RHOA is often reported to be involved in cancer metastasis, including infiltration and migration, rather than carcinogenesis. The high expression of RHOA was observed to contribute to cancer metastasis in experiments using different cancer cell lines including a breast cancer cell line (Non Patent Literature 11).

CITATION LIST

Non Patent Literature

Non Patent Literature 1: J. Surg. Oncol. (2013) 107 (3) 230-6
Non Patent Literature 2: CA Cancer J. Clin. (2011) 61 (2) 69-90
Non Patent Literature 3: Clinical Summary: Reimbursement & Formulary (https://subscriptions.nccn.org/gl_login.aspx?ReturnURL=http://www.nccn.org/professionals/physician_gls/pdf/gastric.pdf)
Non Patent Literature 4: Lancet (2010) 376 (9742) 687-97
Non Patent Literature 5: 2013 GASTROINTESTINAL CANCERS SYMPOSIUM, Result of HER2 status in Japanese metastatic gastric cancer: Prospective cohort study (JFMC44-1101)
Non Patent Literature 6: J. Clin. Oncol. (2011) 29 (30) 3968-76
Non Patent Literature 7: Lancet Oncol. (2013) 14 (6) 490-9
Non Patent Literature 8: Nat. Rev. Cancer (2002) 2 (2) 133-42
Non Patent Literature 9: Biochim. Biophys. Acta. (2009) 1796 (2) 91-8
Non Patent Literature 10: Biochim. Biophys. Acta. (2009) 1795 (2) 137-51
Non Patent Literature 11: Nat. Cell Biol. (2010) 12 (5) 457-67

SUMMARY

Technical Problem

An object of the present invention is to provide a novel method of detecting cancer. Another object of the present invention is to provide a method of screening inhibitors and anticancer agents that target cancer-related molecules. A further object of the present invention is to provide a therapeutic agent for cancer.

Solution to Problem

To solve the above-mentioned problems, the inventors searched for target molecules useful for diagnosis and treatment of cancer and found, among cancer tissue specimens, specimens that have mutations in RHOA which is a molecule belonging to the RAS small GTPase super family. In addition, the inventors observed remarkable cell growth inhibitory effects by suppressing expression of RHOA mutant in cancer cells having RHOA mutations and revealed great contribution of RHOA mutation(s) to cancer cell growth. The present invention provides a method of detecting cancer, especially gastric cancer and/or esophageal cancer, comprising detecting RHOA mutation(s). The present invention also provides a method of treating cancer having RHOA mutation(s) and a method of screening therapeutic agents for cancer. The present invention further provides a therapeutic agent for cancer comprising siRNA that has a silencing effect on a RHOA mutant.

That is to say, the present invention provides the following:
[1] A polypeptide having amino acid mutation(s) of
Arg at position 5,
Gly at position 17,
Leu at position 22,
Val at position 38,
Tyr at position 42,
Glu at position 54, and/or
Tyr at position 74
in the amino acid sequence set forth in SEQ ID NO: 1;
[2] The polypeptide according to [1], wherein
Arg at position 5 is substituted by Trp or Gln,
Gly at position 17 is substituted by Glu,
Leu at position 22 is substituted by Arg,
Val at position 38 is substituted by Gly,
Tyr at position 42 is substituted by Cys,
Glu at position 54 is substituted by Lys, and/or
Tyr at position 74 is substituted by Asp;
[3] A polynucleotide encoding the polypeptide according to [1] or [2];

[4] A vector comprising the polynucleotide according to [3];
[5] A cell comprising the vector according to [4];
[6] A method of screening therapeutic agents for cancer, comprising determining an ability of test substances to inhibit the activation of the polypeptide according to [1] or [2], and selecting test substances having the ability to inhibit as candidates for the therapeutic agents for cancer;
[7] A method of screening therapeutic agents for cancer, comprising contacting a test substance with cells comprising the polypeptide according to [1] or [2] or with the cells according to [5], and monitoring a property of the cells;
[8] The method according to [6] or [7], wherein the cancer comprises cancer cells comprising the polypeptide according to [1] or [2] or the polynucleotide according to [3];
[9] The method according to any one of [6] to [8], wherein the cancer is gastric cancer, colorectal cancer, breast cancer, or lung cancer;
[10] A method of detecting the presence of cancer in a subject, comprising detecting a polypeptide having amino acid mutation(s) of
Arg at position 5,
Gly at position 17,
Leu at position 22,
Val at position 38,
Tyr at position 42,
Glu at position 54, and/or
Tyr at position 74
in the amino acid sequence set forth in SEQ ID NO: 1 or a polynucleotide encoding the polypeptide in a sample separated from the subject;
[11] The detection method according to [10], wherein the amino acid mutation(s) are
a substitution of Trp or Gln for Arg at position 5,
a substitution of Glu for Gly at position 17,
a substitution of Arg for Leu at position 22,
a substitution of Gly for Val at position 38,
a substitution of Cys for Tyr at position 42,
a substitution of Lys for Glu at position 54, and/or
a substitution of Asp for Tyr at position 74;
[12] The method according to [10] or [11], comprising detection by an immunological technique;
[13] The method according to [10] or [11], comprising detection by a technique for detection of gene mutation;
[14] The method according to any one of [10] to [13], wherein the cancer is gastric cancer, colorectal cancer, breast cancer, or lung cancer;
[15] A therapeutic agent for cancer, comprising siRNA that can suppress expression of a polynucleotide encoding a polypeptide having amino acid mutation(s) of
Arg at position 5,
Gly at position 17,
Leu at position 22,
Val at position 38,
Tyr at position 42,
Glu at position 54, and/or
Tyr at position 74
in the amino acid sequence set forth in SEQ ID NO: 1;
[16] The therapeutic agent for cancer according to [15], wherein the siRNA comprises any sequence of SEQ ID NOs: 3 to 12 and SEQ ID NOs: 19 to 22;
[17] The therapeutic agent for cancer according to [15] or [16], wherein the cancer is gastric cancer, colorectal cancer, breast cancer, or lung cancer;
[18] A therapeutic agent for cancer positive for RHOA mutation(s), wherein the therapeutic agent comprises a substance that inhibits function of the polypeptide according to [1] or [2]; and

[19] The therapeutic agent according to [18], wherein the cancer is gastric cancer, colorectal cancer, breast cancer, or lung cancer.

DESCRIPTION

1. Definition

Amino Acid

Figure 1:
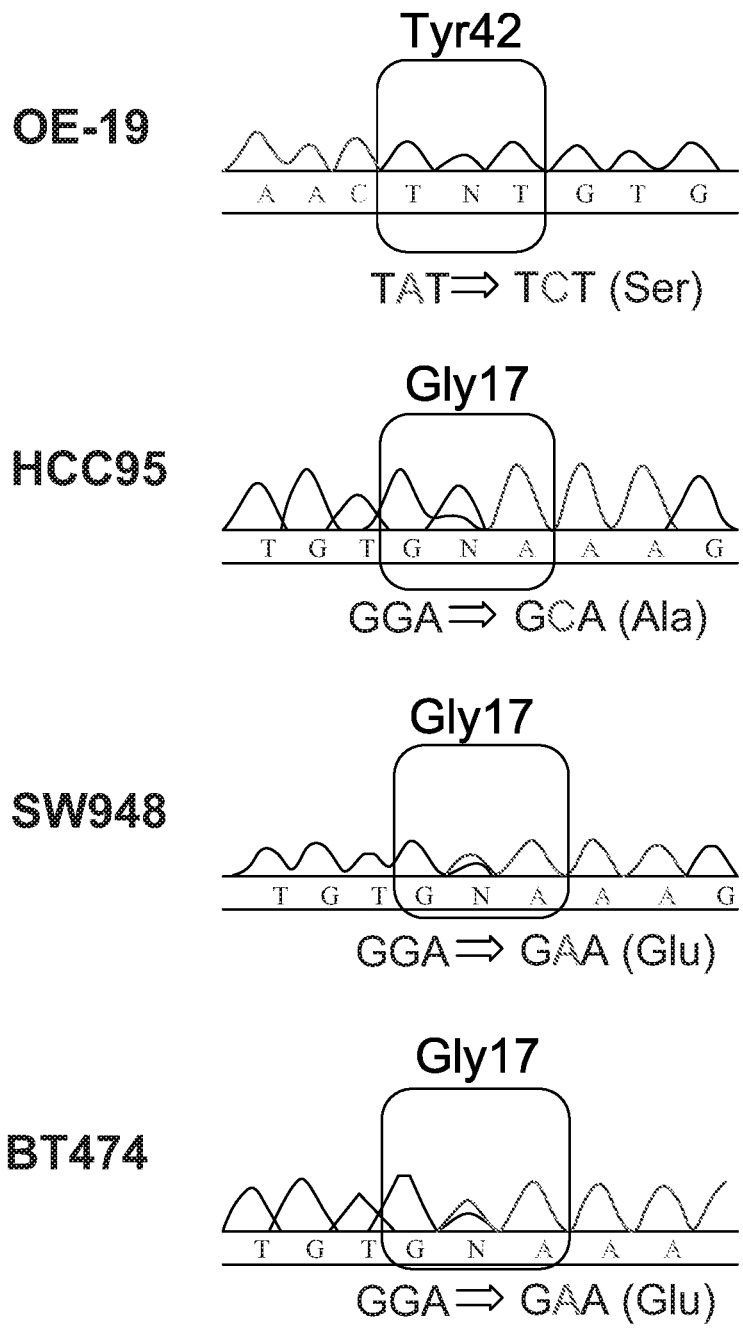
FIG. 1 depicts mutations present at each position of Y42 and G17 in RHOA in cancer cell lines having mutations in RHOA.

Amino acids are represented herein by one letter code or three letter code or both, for example as follows: Ala/A, Leu/L, Arg/R, Lys/K, Asn/N, Met/M, Asp/D, Phe/F, Cys/C, Pro/P, Gln/Q, Ser/S, Glu/E, Thr/T, Gly/G, Trp/W, His/H, Tyr/Y, Ile/I, and Val/V. Amino acids contained in the amino acid sequences as described herein may undergo post-translational modification (such as deamidation of Asn in the amino acid sequence containing Asn-Gly repeats). Even if amino acids undergo post-translational modification, the amino acids are of course included in the amino acid sequences as described herein.

And/or

The term "and/or" as used herein to refer to amino acid mutations includes any suitable combination between "and" and "or". Specifically, for example, "amino acid mutation(s) at position 22, position 38, and/or position 42" includes variations of the following amino acid mutations: (a) position 22, (b) position 38, (c) position 42, (d) position 22 and position 38, (e) position 22 and position 42, (f) position 38 and position 42, and (g) position 22, position 38, and position 42.

GTPase Activity

The term GTPase activity of a substance refers to an activity of hydrolyzing GTP bound to a target polypeptide including the substance itself to GDP. For example, GTPase activity of RHOA set forth in SEQ ID NO: 1 can be determined by the method described in Homma et al. (EMBO J. (1995) 14, 286), that is a method of determining decreased radioactivity of [$\gamma$-$^{32}$P] GTP/GST-RHOA. Commercially available kits for determining GTPase may also be used appropriately.

Rho Family Polypeptide

The term Rho family polypeptide refers to a small membrane-associated Ras-associated GTP-binding protein that functions by binding to and hydrolyzing GTP. RHO family polypeptide serves as a molecular switch that cycles between GDP-bound inactive conformation and GTP-bound active conformation. RHO family is known to include RHOA, RHOB, RHOC, CDC42, RAC1, RAC2, RAC3, TC10, RHOG, RHOD, CHP, WRCH1, TCL and RIF.

Polynucleotide

The term polynucleotide refers to a polynucleic acid that exists in a single- or double-stranded form and in a sense- or antisense-orientation. Polynucleotides include polyribonucleic acid, polydeoxyribonucleic acid, and synthetic analogs thereof. Polynucleotides also include nucleic acids with modified backbones such as peptide nucleic acid (PNA), polysiloxane and 2'-O-(2-methoxy) ethylphosphorothioate. Polynucleotides may be described as sequences with varying length ranged from about 10 to about 5000 bases, especially from about 100 to about 4000 bases, especially from about 250 to about 2500 bases. In one embodiment, polynucleotides are about 10 to about 30 bases in length. In another different non-limiting aspect, polynucleotides are polyribonucleotides with about 17 to about 22 nucleotides, which are more generally referred to as small interfering RNAs (siRNAs). In another non-limiting aspect, polynucleotides include nucleic acids with modified backbones, such as peptide nucleic acid (PNA), polysiloxane, and 2'-O-(2-methoxy)ethylphosphorothioate, non-naturally occurring nucleic acid residues, one or more nucleic acid substituents, such as methyl-, thio-, sulfate-, benzoyl-, phenyl-, amino-, propyl-, chloro- and methanocarba-nucleosides, or nucleic acids with reporter molecules that facilitate detection of the nucleic acids. A polynucleotide is selected herein to be substantially complementary to the opposite strand of a particular target DNA sequence. This means that the polynucleotide must be complementary enough to hybridize with the opposite strand of the target DNA sequence. Polynucleotides include complementary polynucleic acids that hybridize with particular polynucleic acids under stringent conditions and also include polynucleotides comprising base pairs at least about 60 percent, preferably about 70 percent, especially preferably about 80 percent, further preferably about 90 percent, and in a certain aspect, 100 percent identical to the base pairs of the particular polynucleic acids.

The polypeptides or polynucleotides of the present invention are preferably isolated. As used herein, the term "isolated" in the context of the polypeptides or polynucleotides of the present invention refers to a state that is separated from other components with which the polypeptides or polynucleotides are associated in nature. In a non-limiting aspect, the polypeptides or polynucleotides of the present invention are "isolated" when the polypeptides or polynucleotides are at least 50% by weight without other naturally associated polypeptides, peptides and naturally occurring organic molecules or alternatively the polynucleic acids are "isolated" when the polynucleic acids are free from nucleic acid sequences that naturally flank the polynucleic acid sequences in the genome of organism. Preferably, the polypeptides or polynucleotides are at least 75%, preferably 80%, more preferably at least 90% or 95%, and further preferably at least 99% pure by weight. The substantially pure polypeptides or polynucleotides can be obtained by chemical synthesis, isolation of the polypeptides or polynucleotides from natural sources, or production of factors in recombinant host cells that do not naturally produce the polypeptides or polynucleotides.

Compound

The term compound is used herein in the context of "test substances" or "candidates for therapeutic agents" described in respect to screening methods of the present invention. The compounds include organic and inorganic compounds and may be obtained by chemical synthesis or from natural resources. The compounds include inorganic and organic compounds such as polynucleotides, lipids or hormone analogs. Other organic biopolymer compounds include peptides comprising about 2 to about 40 amino acids and larger polypeptides comprising about 40 to about 500 amino acids, and also include polypeptide ligands, polypeptide antagonists, polypeptide agonists, antibodies or antibody conjugates.

Contacting

The term contacting as used herein refers to just adding a specimen comprising an object into another specimen comprising a different object either in vitro or in vivo. For example, contacting test substances with cells means adding a specimen comprising test substances into another specimen comprising cells. Incubating this mixture for a sufficient time without defining contacting time allows observation of the effect of the test substances on the cells.

Assay

The term assay refers to any process used for measuring a certain property of compounds. The term screening method refers to a method used for characterizing or selecting compounds from a collection of compounds based on the activities of the compounds.

Inhibition

The term inhibition refers to decrease in processes, downregulation, or elimination of stimulus in processes. A non-limiting aspect of the inhibition is absence or minimization of expression or activity of polypeptides.

Sample Isolated from a Subject

Subjects used in the detection method of the present invention include generally accepted animals including human and other mammals. As used herein, a sample separated from a subject, which is expected to comprise RHOA mutants of the present invention or polynucleotides encoding thereof, refers to any liquid or solid sample separated from a subject. The sample may often be a clinical sample, i.e., a sample obtained or isolated from patients to be examined for cancer. The sample includes, but is not limited to, body fluids that comprise cellular materials and can comprise cells, for example, blood, plasma, serum, urine, semen, saliva, ocular lens fluid, and lymphatic fluid, and tissue samples separated from digestive organs such as stomach, esophagus, and rectum. The sample may also be a section of the tissue samples.

2. RHOA Mutant

The RHOA mutant according to the present invention represents a polypeptide in which at least one of amino acids composing the polypeptide is mutated from the amino acid sequence of naturally occurring RHOA. The RHOA mutant has preferably a GTPase activity. A non-limiting aspect of the amino acid sequence of naturally occurring RHOA may be the amino acid sequence set forth in SEQ ID NO: 1 (NP_001655.1). An aspect of the mutation may include mutations of amino acids contained in the functional domains involved in GTP linkages that correspond to positions 12 to 19, positions 59 to 63, and/or positions 117 to 120 in the amino acid sequence set forth in SEQ ID NO: 1 (http://www.uniprot.org/uniprot/P61586, Ridley (Int. J. Biochem. Cell. Biol. (1997) 29 (11) 1225-9)). Examples of the mutation may also include mutations of amino acids contained in the functional domain, which corresponds to positions 34 to 42 in the amino acid sequence set forth in SEQ ID NO: 1, involved in binding of effector molecules participated in signal transduction (http://www.uniprot.org/uniprot/P61586, Vega et al. (FEBS Lett. (2008) 582 (14) 2093-101)). The functional domain, which corresponds to positions 34 to 42 in the amino acid sequence set forth in SEQ ID NO: 1, involved in binding of effector molecules participated in signal transduction is also called as switch I (http://www.uniprot.org/uniprot/P61586, Vega et al. (FEBS Lett. (2008) 582 (14) 2093-101)). The conformations of GDP-bound inactive RHOA and GTP-bound active RHOA are significantly different from each other. Such a conformational change is known to play an important role in binding of effector molecules (Vega et al. (FEBS Lett. (2008) 582 (14) 2093-101)).

An aspect of the mutation include mutation(s) of Arg at position 5, Gly at position 17, Leu at position 22, Val at position 38, Tyr at position 42, Glu at position 54, and/or Tyr at position 74 in the amino acid sequence set forth in SEQ ID NO: 1. Examples of the mutations may include deletion, substitution, and addition at the amino acid positions. The mutations may be preferably substitution of the amino acids as described above. A non-limiting aspect of the substitution may include a substitution of Trp or Gln for Arg at position 5, a substitution of Glu for Gly at position 17, a substitution of Arg for Leu at position 22, a substitution of Gly for Val at position 38, a substitution of Cys for Tyr at position 42, a substitution of Lys for Glu at position 54, and/or a substitution of Asp for Tyr at position 74. It is noted that the mutations or substitutions of amino acids in the present invention means mutations or substitutions of amino acid residues in polypeptides.

The present invention also provides a polynucleotide encoding a polypeptide having mutations at the following amino acid(s): Arg at position 5, Gly at position 17, Leu at position 22, Val at position 38, Tyr at position 42, Glu at position 54, and/or Tyr at position 74 in the amino acid sequence set forth in SEQ ID NO: 1. Examples of the mutations may include deletion, substitution, and addition at the amino acid positions. The mutations may be preferably substitution of the amino acids as described above. A non-limiting aspect of the substitution may include a substitution of Trp or Gln for Arg at position 5, a substitution of Glu for Gly at position 17, a substitution of Arg for Leu at position 22, a substitution of Gly for Val at position 38, a substitution of Cys for Tyr at position 42, a substitution of Lys for Glu at position 54, and/or a substitution of Asp for Tyr at position 74.

As used herein, the phrase positive for RHOA mutation(s) refers to a positive detection result for the presence of a RHOA mutant polypeptide having amino acid mutation(s) as described above or a polynucleotide encoding thereof.

3. Methods of Detecting Cancer

The present invention provides a method of detecting the presence of cancer in a subject, comprising detecting RHOA mutant polypeptides of the present invention or polynucleotides encoding thereof in a sample separated from the subject. Since the RHOA mutants have been proved to be found in tumor sites of gastric cancer, esophageal cancer, and/or scirrhous gastric cancer, detection of the presence of the RHOA mutant in a sample separated from a subject leads to detection of the presence of cancer, preferably gastric cancer, esophageal cancer, and/or scirrhous gastric cancer in the subject. Although the quantitative alteration of a RHOA polypeptide including enhanced expression of the RHOA polypeptide set forth in SEQ ID NO: 1 has been previously known in some cancers, the qualitative alteration of a RHOA polypeptide that is found in the present invention, which is the expression of the RHOA mutants according to the present invention in some cancers, preferably gastric cancer, esophageal cancer, and/or scirrhous gastric cancer, is an unexpected discovery. Accordingly, the present invention provides a method of detecting the presence of cancer, suitably gastric cancer, esophageal cancer, and/or scirrhous gastric cancer in a subject by detecting the qualitative alteration of RHOA.

Immunological Techniques

Immunological techniques for detecting RHOA mutant polypeptides of the present invention include antibodies that can bind the polypeptides, for example, antibodies with detectable labels. Preferably, the antibodies hardly bind wild type RHOA or do not bind wild type RHOA at all. The antibodies may be polyclonal or monoclonal. Complete antibodies or fragments thereof (such as Fab or F(ab')2) can also be used. Examples of labeling of antibodies include direct labeling by linking an antibody to a detectable label or indirect labeling by reacting an antibody with another reagent directly labeled. Examples of the indirect labeling include detection of a primary antibody using a fluorescently labeled secondary antibody.

In another non-limiting aspect, antibodies may be labeled with, for example, radioactive substances, chromophores, fluorophores, or enzymes. In another embodiment, antibody derivatives (such as an antibody or fragments thereof (such as single-chain antibodies and isolated antibody variable regions) linked to a substrate or either one of a pair of ligands such as, for example, biotin-streptavidin) may be used.

Immunohistochemistry (IHC) refers to a method of detecting antigens present in tissue sections by utilizing the principle of antibodies that specifically bind antigens in biological tissues. Immunohistochemical staining has been widely used in diagnosis of abnormal cells with specific molecular markers found in cancer tissues or tumors. The markers indicate characteristics of phenomena, such as carcinogenesis (transformation) and cell death (apoptosis), in specific cells. IHC has been also widely used in studies for understanding distribution and localization of markers present in different locations of a biological tissue as well as differentially expressed proteins. Interaction between an antibody and an antigen can be visualized with many methods. In the most common example, an antibody is linked to an enzyme such as peroxidase which can catalyze color reaction. In other non-limiting aspect, an antibody is linked to a fluorophore tag (such as a fluorescein, a rhodamine, DyLight Fluor, or Alexa Fluor).

In another non-limiting aspect, RHOA mutants of the present invention expressed in tissues or cells in living organisms can be also detected by some methods such as Western blot and immunofluorescence techniques using antibodies or antibody fragments. Samples can be isolated from the tissues or cells using techniques known to those having an ordinary level of skill in the art. For example, methods of isolating a protein fraction comprising polypeptides subject to detection include a method described by Harlow and Lane (Harlow and Lane, 1988, Antibodies: A Laboratory Manual, Cold Spring Harbor Laboratory Press, Cold Spring Harbor, N.Y.). In such aspects, antibodies or polypeptides can be immobilized on solid supports. Suitable solid phase supports or carriers may include any support that can bind the polypeptides or antibodies. Known supports or carriers include glass, polystyrene, polypropylene, polyethylene, dextran, nylon, natural or modified cellulose, polyacrylamide, and magnetite.

Many other suitable carriers for binding antibodies or antigens are known to those having an ordinary level of skill in the art. Such supports may be used for detection methods of the present invention. For example, protein fractions isolated from cells can be subject to polyacrylamide gel electrophoresis and polypeptides contained in the fractions can be immobilized on solid phase supports (such as nitrocellulose). The supports, after washed with a suitable buffer, can be then treated with a detectably labeled antibody. After removing unbound antibodies from the supports by washing with the buffer twice, the amount of label bound to the solid phase supports can be determined by any known means. Protein detection means using electrophoresis techniques are known to those having an ordinary level of skill in the art (Harlow and Lane, supra).

In another non-limiting aspect, Western blot (immunoblot) analysis can be used to detect the presence of and quantify polypeptides in a sample. The technique generally comprises separating polypeptides contained in the sample by gel electrophoresis based on the molecular weights of the polypeptides, transferring the separated polypeptides to any suitable solid phase support (such as a nitrocellulose filter, a nylon filter, or a derivatized nylon filter), and incubating the sample with an antibody that specifically binds a polypeptide. Anti-RHOA mutant polypeptide antibodies can specifically bind RHOA mutant polypeptides on solid phase supports. The antibodies can be directly labeled or can be detected by another labeled antibody that specifically binds anti-RHOA mutant polypeptide antibody (such as a labeled sheep anti-mouse antibody).

Antibodies that specifically bind RHOA mutant polypeptides can be obtained using any known method. Examples of suitable antibodies used in the present invention can include polyclonal or monoclonal antibodies or fragments thereof. For example, monoclonal antibodies can be prepared with hybridoma techniques as taught by Hammerling et al. (Monoclonal Antibodies and T-Cell Hybridomas, Elsevier, New York, 1981). In this technique, immunocompetent animals such as mice are immunized with RHOA mutant polypeptides or peptides derived therefrom. Splenocytes extracted from the immunized animals are then fused with suitable myeloma cells such as SP2/0 cells. The cell fusion results in hybridoma cells. The hybridoma cells are selectively maintained in HAT medium and cloned by limiting dilution. The cells obtained through the selection can be then assayed for identifying clones that secrete antibodies that preferentially bind the RHOA mutant polypeptide of the present invention and hardly bind wild type RHOA or do not bind wild type RHOA at all.

Animals will be immunized with the RHOA mutant polypeptides or peptides derived therefrom having for example a mutation of Tyr at position 42 to obtain an antibody that specifically binds the RHOA mutant polypeptide having the mutation of Tyr at position 42 among polypeptides having amino acid mutation(s) of Arg at position 5, Gly at position 17, Leu at position 22, Val at position 38, Tyr at position 42, Glu at position 54, and/or Tyr at position 74 in the amino acid sequence set forth in SEQ ID NO: 1. The length of peptides subject to immunization may be appropriately adjusted. Preferably, the peptides having a mutation of Tyr at position 42 consisting of 5 to 20 amino acids will be used. In a non-limiting aspect, when the mutation at position 42 is a substitution of Cys for Tyr, peptides including TVFENC (SEQ ID NO:25), VFENCV (SEQ ID NO:26), FENCVA (SEQ ID NO:27), ENCVAD (SEQ ID NO:28), NCVADI (SEQ ID NO:29), or CVADIE (SEQ ID NO:30) may be used as a peptide that will be subject to immunization and/or will be used in assays for identifying the clones. When peptides consisting of 10 amino acids are used, peptides including VYVPTVFENC (SEQ ID NO:31), YVPTVFENCV (SEQ ID NO:32), VPTVFENCVA (SEQ ID NO:33), PTVFENCVAD (SEQ ID NO:34), or TVFENCVADI (SEQ ID NO:35) may also be used.

Gene Mutation Detection Techniques

The present invention provides a polynucleotide encoding a polypeptide having amino acid mutation(s) contained in the functional domain, which corresponds to positions 12 to 19, positions 59 to 63, and/or positions 117 to 120 in the amino acid sequence set forth in SEQ ID NO: 1, involved in GTP linkages. The present invention also provides a polynucleotide encoding a polypeptide having amino acid mutation(s) contained in the functional domain, which corresponds to positions 34 to 42 in the amino acid sequence set forth in SEQ ID NO: 1, involved in binding of effector molecules participated in signal transduction. The functional domain, which corresponds to positions 34 to 42 in the amino acid sequence set forth in SEQ ID NO: 1, involved in binding of effector molecules participated in signal transduction is also called as switch I. The conformations of GDP-bound inactive RHOA and GTP-bound active RHOA are different from each other. Such a conformational change is known to play an important role in binding of effector molecules.

The present invention also provides a polynucleotide encoding a polypeptide having mutations of Arg at position 5, Gly at position 17, Leu at position 22, Val at position 38, Tyr at position 42, Glu at position 54, and/or Tyr at position 74 in the amino acid sequence set forth in SEQ ID NO: 1. Examples of the mutations may include deletion, substitution, and addition at the amino acid positions. The mutations may be preferably substitutions of the amino acids. In a non-limiting aspect, the substitutions may include a substitution of Trp or Gln for Arg at position 5, a substitution of Glu for Gly at position 17, a substitution of Arg for Leu at position 22, a substitution of Gly for Val at position 38, a substitution of Cys for Tyr at position 42, a substitution of Lys for Glu at position 54, and/or a substitution of Asp for Tyr at position 74.

The present invention also provides a primer and probe for detecting a polynucleotide encoding a polypeptide having amino acid mutation(s) of Arg at position 5, Gly at position 17, Leu at position 22, Val at position 38, Tyr at position 42, Glu at position 54, and/or Tyr at position 74 in the amino acid sequence set forth in SEQ ID NO: 1. The primer and probe can detect the presence or absence of a gene mutation that results in the mutation in SEQ ID NO: 2 (NM 001664.2). More specifically, the present invention provides an isolated polynucleic acid and use thereof, wherein the isolated polynucleic acid is a polynucleotide sequence set forth in SEQ ID NO: 2 having nucleotide mutations corresponding to the amino acid mutations as described above, which is a nucleotide sequence with at least 10, 12, 15, 20, 30, 40, or 50 consecutive bases (such as a nucleotide with 10 to 30 bases or a nucleotide with 10 to 25 bases), for example a nucleotide with 10 to 30 bases.

These nucleotides can be used to detect the mutations by a variety of methods as described in, for example, WO2003/023063. Examples of the method include RFLP method, PCR-SSCP method, ASO hybridization, direct sequencing method, ARMS method, denaturing gradient gel electrophoresis, RNaseA digestion method, chemical cleavage method, DOL method, TaqMan PCR method, invader method, MALDI-TOF/MS method, TDI method, molecular beacon method, dynamic allele-specific hybridization method, padlock probe method, UCAN method, nucleic acid hybridization methods using DNA chip or DNA microarray, and ECA method.

TaqMan PCR method, which is a non-limiting aspect of the detection method of the present invention, will be described below. TaqMan PCR method uses a mutation-specific oligonucleotide that is fluorescently labeled (TaqMan primer) and PCR using a Taq DNA polymerase. TaqMan primer is an oligonucleotide that is a subsequence from the polynucleotide sequence set forth in SEQ ID NO: 2 and consists of a base sequence with about 15 to about 30 consecutive bases comprising base(s) corresponding to any mutation as described above. The primer has the 5'-end labeled with a fluorescent dye such as FAM and VIC and the 3'-end labeled with a quencher (quenching agent) such as TAMRA. Unless the primer is cleaved, the quencher absorbs fluorescence energy and prevents detection of the fluorescence. The 3'-end of the TaqMan primer is also phosphorylated so as to inhibit PCR elongation from the primer. When PCR is performed using a PCR primer and a Taq DNA polymerase that are designed to amplify a subsequence of mRNA or genomic DNA comprising a polynucleotide that encodes a RHOA mutant polypeptide and hybridizes with the TaqMan primer, the TaqMan primer hybridizes with a template DNA and elongation occurs from the PCR primer simultaneously. As the elongation proceeds, the hybridized TaqMan primer will be cleaved by 5' nuclease activity of the Taq DNA polymerase and the fluorescent dye will be released to achieve detection of fluorescence due to elimination of the effect of quencher. The exponentially increased fluorescence intensity that resulted from amplification of the template can be measured to detect the RHOA mutant of the present invention that specifically hybridizes with the TaqMan primer.

4. Method of Identifying Compounds

In a non-limiting aspect, the present invention relates to a method of identifying compounds that inhibit or facilitate the function of the RHOA mutant according to the present invention, or inhibit or facilitate the expression of the polynucleotide encoding the RHOA mutant according to the present invention. The RHOA mutants have been proved to be found in tumor sites of gastric cancer, esophageal cancer, and/or scirrhous gastric cancer. In the present invention, compounds that inhibit the function of the RHOA mutants and/or inhibit the expression of the polynucleotide encoding the RHOA mutant are identified to provide a therapeutic agent that comprises the identified compounds and thus prevents and/or treats the progression of tumors including gastric cancer, esophageal cancer, and/or scirrhous gastric cancer. Although the quantitative alteration including enhanced expression of the RHOA polypeptide set forth in SEQ ID NO: 1 has been previously known in some cancers, the qualitative alteration of the RHOA polypeptide, which is found in the present invention and is the expression of the RHOA mutants according to the present invention in some cancers, preferably gastric cancer, esophageal cancer, and/or scirrhous gastric cancer, is an unexpected discovery. Accordingly, the present invention provides a therapeutic agent that prevents the progression of and/or treats cancer, preferably gastric cancer, esophageal cancer, and/or scirrhous gastric cancer in a subject by administering the compound that targets RHOA with the qualitative alteration. Preferably, the therapeutic agent of the present invention does not inhibit the function of wild type RHOA set forth in SEQ ID NO: 1.

Therefore, the methods of identifying compounds that are contained in the therapeutic agents in the present invention include preferably a method of screening compounds that inhibit function of the RHOA mutant and/or compounds that inhibit expression of the polynucleotide encoding the RHOA mutant.

The identification method according to the present invention can be performed using a technique to screen pharmaceutical preparations. The technique is known per se and uses at least any one of or a combination of the RHOA mutant, a polynucleotide encoding the mutant, a recombinant vector comprising the polynucleotide, cells that are transformed with the vector or cells that endogenously comprise the RHOA mutant, and an antibody that can specifically bind the RHOA mutant. The identification method may be performed in a test tube (in vitro) or within an organism (in vivo). The identification method can be utilized in a method of screening antagonists in drug design based on the conformation of the RHOA mutant, a method of screening inhibitors, which inhibit expression at the level of genes by utilizing a polypeptide synthesis system, or a method of screening antibody-binding substances using an antibody.

In a non-limiting aspect, the method of identifying compounds that inhibit or facilitate function of the RHOA mutant according to the present invention can be performed by combining cells that are transformed with the vector according to the present invention or cells that endogenously comprise the RHOA mutant with a compound to be tested (test substance) under the condition that allows interaction between the cells and the test substance in an experimental system that can determine function of the RHOA mutant; determining function of the cells; comparing the function of the cells under the presence of the test substance and the function of the cells under the absence of the test substance with each other, and each also with either the function of the cells that do not comprise the vector according to the present invention or with the function of the cells that do not endogenously comprise the RHOA mutant; and detecting the presence or absence, or alteration, such as decrease, increase, disappearance, and appearance, of the function of the RHOA mutant. When the function of the RHOA mutant decreases or disappears under the presence of the test substance as compared with the function of the RHOA mutant under the absence of the test substance, the test substance can be determined to inhibit the function of the RHOA mutant. In contrast, when the function of the RHOA mutant increases under the presence of the test substance, the test substance can be determined to facilitate the function of the RHOA mutant. The functions can be determined by directly detecting the function or by putting a signal, which is indicative of the function, into the experimental system and detecting the signal. Examples of the signal can include enzymes such as GST, tag peptides such as His-tag, Myc-tag, HA-tag, FLAG-tag, or Xpress-tag, or fluorescent proteins. Any labeling substance commonly used in methods of identifying compounds may be used.

A non-limiting aspect of the cell function that can be used in the direct detection is focus-forming ability. The focus-forming ability is utilized in focus forming assay. Focus forming assay is performed using, for example, suitable cells (such as NIH3 T3 cell line stably transduced with the RHOA mutant according to the present invention and OE19 cell line endogenously expressing the RHOA mutant according to the present invention) seeded at $5 \times 10^4$ cells per 6-well plate and maintained for 15 to 21 days in 10% FBS. The medium will be exchanged for a fresh medium every 2 to 3 days. After staining with crystal violet (1%), the plate will be photographed and focuses will be measured using MetamMorph® software.

Another non-limiting aspect of the cell function that can be used in the direct detection is anchorage-independent growth ability. To assay the ability, a variety of suitable cells (such as NIH3T3 cell line stably transduced with the RHOA mutant according to the present invention and OE19 cell line endogenously expressing the RHOA mutant according to the present invention) are seeded at $1.25 \times 10^3$ cells/well in a 6-well plate. After 3 to 5 weeks, the number of colonies grown in 0.3% agarose is counted. One ml of top agarose is added to each well once a week after seeding.

The method of identifying compounds that inhibit or facilitate the function of the RHOA mutant according to the present invention can be performed by combining the RHOA mutant with a compound to be tested (test substance) under the condition that allows the interaction between the RHOA mutant and the test substance in an experimental system that can determine the function of the RHOA mutant; determining the function of the mutant; comparing the function of the RHOA mutant under the presence of the test substance with the function of the RHOA mutant under the absence of the test substance; and detecting the presence or absence, or alteration, such as decrease, increase, disappearance, and appearance, of the function of the RHOA mutant. When the function of the RHOA mutant decreases or disappears under the presence of the test substance as compared with the function of the RHOA mutant under the absence of the test substances, the test substance can be determined to inhibit the function of the RHOA mutant. In contrast, when the function of the RHOA mutant increases under the presence of the test substance, the test substance can be determined to facilitate the function of the RHOA mutant. The functions can be determined by directly detecting the function or by putting a signal, which is indicative of the function, into the experimental system and detecting the signal. Examples of the signal can include enzymes such as GST, tag peptides such as His-tag, Myc-tag, HA-tag, FLAG-tag, and Xpress-tag, and fluorescent proteins. Any labeling substance commonly used in the methods of identifying compounds may be used.

A non-limiting aspect of the method of identifying compounds that inhibit or facilitate the functions of the RHOA mutant according to the present invention is a method of identifying compounds using the expression of a polynucleotide encoding the RHOA mutant according to the present invention as a criterion. In aspects wherein the expression of a polynucleotide encoding the RHOA mutant according to the present invention is used as a criterion, compounds with the desired properties can be identified by combining the polynucleotide with a test substance under the condition that allows interaction between the polynucleotide and the test substance in an experimental system that can determine the expression of the polynucleotide; determining the expression of the polynucleotide; comparing the expression of the polynucleotide under the presence of the test substance with the expression of the polynucleotide under the absence of the test substance; and detecting the presence or absence, or alteration, such as decrease, increase, disappearance, and appearance, of the expression of the polynucleotide. When the expression of the polynucleotide decreases or disappears under the presence of the test substance as compared with the expression of the polynucleotide under the absence of the test substance, the test substance can be determined to inhibit the expression of the polynucleotide. In contrast, when the expression of the polynucleotide increases under the presence of the test substance, the test substance can be determined to facilitate the expression of the polynucleotide.

Specifically, in aspects wherein the expression of the polynucleotide according to the present invention is used as a criterion, compounds with the desired properties can be identified for example by contacting a transformant according to the present invention with the test substance in an experimental system in which the transformant is used to express the polynucleotide; and then measuring the expression of the polynucleotide. The expression can be measured by using as a criterion the amount of the expressed RHOA mutant polypeptide according to the present invention or the amount of mRNA encoding the polypeptide, or the function of the RHOA. The expression can also be measured for example by putting a signal, which is indicative of the expression, into the experimental system and detecting the signal. Examples of the signal include enzymes such as GST, tag peptides such as His-tag, Myc-tag, HA-tag, FLAG-tag, or Xpress-tag, and fluorescent substances. The methods of detecting these signals are well known to those having an ordinary level of skill in the art.

5. Compounds Inhibiting or Facilitating the Function of the RHOA Mutant

The compounds selected by the identification method according to the present invention can be used as candidate compounds for inhibitors for the expression of the polynucleotide according to the present invention, or for inhibitors or antagonists for the function of the RHOA mutant according to the present invention. The compounds obtained by the identification method can be used as candidate compounds for promoters for the expression of the polynucleotide according to the present invention or for promoters for the function of the RHOA mutant according to the present invention. Since the RHOA mutants according to the present invention have been proved to be found in tumor sites of gastric cancer, esophageal cancer, and/or scirrhous gastric cancer, the inventors have expected that these diseases can be prevented and/or treated by inhibiting the function of the RHOA mutant according to the present invention and/or by inhibiting the expression of the polynucleotide. Accordingly, compounds obtained by the identification method according to the present invention preferably include compounds inhibiting the function of the RHOA mutant according to the present invention and/or compounds inhibiting the expression of the polynucleotide. These candidate compounds will be selected by taking into account the balance between their benefits and toxicity to be prepared for medicaments. These medicaments are effective in prevention and/or treatment of various pathological conditions caused by abnormal function of RHOA mutant according to the present invention and/or abnormal expression of the polynucleotide. The compounds according to the present invention include compounds that are obtained by a method other than the identification method and that inhibit the function of the RHOA mutant according to the present invention and/or inhibit the expression of the polynucleotide, or that facilitate the function of the RHOA mutant according to the present invention and/or facilitate the expression of the polynucleotide.

Therapeutic Agent for Cancer Comprising a Substance that Inhibits the Function of the RHOA Mutant The present invention includes a therapeutic agent for cancer positive for RHOA mutation(s), wherein the therapeutic agent comprises, as an active ingredient, a substance that inhibits the function of the RHOA mutant (such as a substance obtained by the screening method of the present invention (such as a double-stranded nucleic acid (including siRNA), a protein (including an antibody and an antibody fragment), a peptide, or other compounds)).

Active principles in the therapeutic agent for cancer of the present invention can be selected by the screening method of the present invention (see "Method of identifying compounds" above). Preferably, the therapeutic agent of the present invention does not inhibit the function of wild type RHOA set forth in SEQ ID NO: 1.

Formulations comprising, as an active ingredient, a substance that inhibits the function of the RHOA mutant of the present invention (such as a substance obtained by the screening method of the present invention (such as a double-stranded nucleic acid, a protein (including an antibody or an antibody fragment), a peptide, or other compounds)) can be prepared in the form of pharmaceutical compositions with pharmacologically acceptable carriers, excipients, and/or other additives commonly used in the formulation depending on the type of the active ingredient.

Subjects to be treated with the therapeutic agent for cancer of the present invention are subjects in whom the presence of the polynucleotide and/or polypeptide of the present invention is detected (i.e., patients with cancer positive for RHOA mutation(s) of the present invention). Since the RHOA mutants according to the present invention have been proved to be found in tumor sites of gastric cancer, esophageal cancer, and/or scirrhous gastric cancer, the inventors have expected that these diseases can be prevented and/or treated by inhibiting the function of the RHOA mutant according to the present invention. Therefore, the substance that inhibits the function of the RHOA mutant of the present invention will be an effective therapeutic agent for cancer positive for RHOA mutation(s) of the present invention (especially gastric cancer, esophageal cancer, and/or scirrhous gastric cancer).

Therapeutic Agent Comprising RNA Utilized for siRNA

A double stranded RNA (dsRNA) is shown to have a potent and specific silencing effect on gene expression in non-mammalian cells, which is referred to as RNA interference (RNAi) (Sharp (Genes Dev. (1999) 13 (2) 139)). A dsRNA is processed by an enzyme having the RNAseIII motif into shorter dsRNAs having 20 to 23 nucleotides, which are referred to as small interfering RNA (siRNA). siRNAs specifically target mRNAs complementary to the siRNAs via multicomponent nuclease complexes (Hammond et al. (Nature (2000) 404 (6775) 293)). An siRNA consisting of 20- or 21-mer dsRNA comprising 19 base-paired nucleotides and two non-base-paired nucleotides, each of which non-base-paired nucleotides is thymidine or uridine, at the 3'-end is shown to have a gene-specific knockdown effect without inducing the overall alteration of gene expression in mammalian cells (Elbashir et al. (Nature (2001) 411 (6836) 494)). Moreover, a plasmid comprising small nuclear RNA (snRNA) U6 or polymerase III H1-RNA promoter can efficiently produce a small RNA that recruits RNA polymerase III to result in constitutive suppression of the target mRNA (Miyagishi et al. (Nat. Biotechnol. (2002) 20 (5) 497)).

Cell growth is inhibited by contacting cells with a composition comprising siRNA having a silencing effect on the RHOA mutant of the present invention. The cells are further contacted with a transfection reagent. Suitable transfection reagents are known in the art. The term "inhibition of cell growth" means cell growth rate or survival rate lower than that in the cells without exposure to the composition. The cell growth can be measured by any method known in the art such as MTT cell growth assay.

siRNA, which is hybridized with a target mRNA, against the RHOA mutant of the present invention usually binds a single-stranded mRNA transcript to inhibit the translation and thus inhibit the protein expression. This inhibition will decrease or prevent production of the RHOA mutant polypeptide of the present invention encoded by the RHOA mutant gene. The siRNA molecule of the present invention can be defined by an ability for the siRNA to specifically hybridize with mRNA or cDNA derived from the RHOA mutant gene of the present invention. For the purpose of the present invention, the term "hybridize" or "specifically hybridize" is used to refer to hybridization between two nucleic acid molecules under a "stringent hybridization condition". The term "stringent hybridization condition" typically refers to a condition in which a nucleic acid molecule hybridizes with the target sequence in a complex mixture of nucleic acids but does not detectably hybridize with any other sequence. Stringent conditions are sequence-dependent and vary in different circumstances. Longer sequences specifically hybridize at higher temperature. Generally, stringent conditions are selected to be about 5 to 10° C. lower than the thermal melting point (Tm) for the specific sequence at a defined ionic strength and pH. Tm is the temperature (under defined ionic strength, pH, and nucleic acid concentration) at which 50% of the probes complementary to the target sequence hybridize with the target sequence at equilibrium (when the target sequences are present in excess, at Tm, 50% of the probes are occupied at equilibrium). Stringent conditions can also be achieved with the addition of destabilizing agents such as formamide. In a selective or specific hybridization, a positive signal is at least twice as strong as that in background, preferably 10 times as strong as that in background hybridization. An exemplary stringent hybridization condition may be as follows: incubation in 50% formamide, 5×SSC, and 1% SDS at 42° C. or incubation in 5×SSC and 1% SDS at 65° C. followed by washing in 0.2×SSC and 0.1% SDS at 50° C.

The siRNA of the present invention is less than about 500, about 200, about 100, about 50, or about 25 nucleotides in length. The siRNA is preferably about 19 to about 25 nucleotides in length. Exemplary nucleic acid sequences for producing siRNA specific for the RHOA mutant of the present invention include a sequence that targets the nucleotide sequence of SEQ ID NO: 2 having nucleotide mutations corresponding to amino acid mutation(s) in the mutant of the present invention. To increase the inhibitory activity of the siRNA, nucleotide "U" may be added to the 3'-end of the antisense strand of the target sequence. The number of "Us" to be added is at least about 2, generally about 2 to about 10, preferably about 2 to about 5. Added "Us" form a single strand at the 3'-end of the antisense strand of siRNA.

The cell is any cancer cell expressing the RHOA mutant of the present invention. The cancer cell may be present in esophageal cancer tissue and gastric cancer tissue. The cancer cell may be present in scirrhous gastric cancer tissue.

The siRNA specific for the RHOA mutant of the present invention will be directly transduced into cells while keeping a form that allows the siRNA to bind mRNA transcript. Alternatively, DNA encoding the siRNA specific for the RHOA mutant of the present invention may be incorporated in a vector as described below.

The vector is an expression vector that is produced, for example, by operably linking target sequences contained in the RHOA mutant sequence of the present invention to regulatory sequences flanking the RHOA target sequences so as to enable both sense and antisense strands to be expressed (by transcription of DNA molecule) (Lee et al. (Nat. Biotechnol. (2002) 20, 500)). One RNA molecule, which is an antisense strand for the RHOA mutant mRNA of the present invention, is transcribed from the first promoter (such as a promoter sequence positioned 3' to the cloned DNA) and another RNA molecule, which is a sense strand for the RHOA mutant mRNA of the present invention, is transcribed from the second promoter (such as a promoter sequence positioned 5' to the cloned DNA). The sense and antisense strands hybridize each other in vivo to form an siRNA construct for silencing the RHOA mutant gene of the present invention. Alternatively, two constructs may be used for the production of sense and antisense strands of an siRNA construct. The cloned RHOA mutant gene of the present invention can be transcribed into a RNA construct with secondary structure. The secondary structure is for example a hairpin structure that is formed by a single transcript and that has a sense sequence from a target gene and an antisense sequence complementary to the sense sequence. To form a hairpin loop structure, the loop sequence consisting of any nucleotide sequence can be positioned between the sense sequence and the antisense sequence. Accordingly, the present invention also provides an siRNA with a general formula 5'-[A]-[B]-[A']-3', wherein [A] represents a ribonucleotide sequence corresponding to a sequence that specifically hybridizes with mRNA or cDNA derived from the RHOA mutant gene of the present invention. In preferred aspects, [A] represents the ribonucleotide sequence corresponding to a sequence selected from the group consisting of nucleotide sequences set forth in SEQ ID NO: 2 having nucleotide mutations corresponding to the amino acid mutations in the mutant of the present invention. [B] represents a ribonucleotide sequence consisting of 3 to 23 nucleotides and [A'] represents a ribonucleotide sequence consisting of a sequence complementary to [A]. The domain [A] hybridizes with [A'] and then forms a loop structure consisting of domain [B]. The loop sequence can be preferably about 3 to about 23 nucleotides in length. For example, the loop sequence can be selected from the group consisting of the following sequences. For example, preferred siRNAs with hairpin loop structure of the present invention are listed below. The loop sequence can be selected from the group consisting of, but not limited to, CCC, CCACC, CCACACC (Jacque et al. (Nature (2002) 418, 435)), UUCG (Lee et al. (Nat. Biotechnol. (2002) 20 500) and Fruscoloni et al. (Proc. Natl. Acad. Sci. USA (2003) 100, 1639)), and UUCAAGAGA (Dykxhoorn et al. (Nat. Rev. Mol. Cell Biol. (2003) 4, 457). Further, loop sequences consisting of 23 nucleotides also provide active siRNAs (Jacque et al. (Nature (2002) 418, 435)).

The sense strand and antisense strand can be appropriately designed using any known software or program. Such programs are provided, for example, in the web sites of manufacturers of siRNA molecules listed below.
http://rnaidesigner.invitrogen.com/rnaiexpress/
http://www.invitrogen.com/site/us/en/home/Products-and-Services/Applications/rnai.html
http://www.thermoscientificbio.com/design-center/
http://sidirect2.rnai.jp/
http://optirna.unl.edu/
http://biotools.idtdna.com/Scitools/Applications/RNAURNAi.aspx?source=menu
http://sfold.wadsworth.org/cgi-bin/sirna.pl
http://sysbio.kribb.re.kr:8080/AsiDesigner/menuDesigner.jsf, and
http://sirna.wi.mit.edu/.

In a non-limiting aspect, the following sequences can be suitably used for the sequence of the domain [A] as described above:

```
                                           (SEQ ID NO: 3)
    si1: GAAAGACAUGCUUGCUCAUAGUCUU (SEQ ID NO: 4)
    si2: CAGAGGUGUAUGUGCCCACAGUGUU (SEQ ID NO: 5)
    si3: UGUUUGAGAACUAUGUGGCAGAUAU (SEQ ID NO: 6)
    si4: UGGCAGAUAUCGAGGUGGAUGGAAA (SEQ ID NO: 7)
    si5: UCGAGGUGGAUGGAAAGCAGGUAGA (SEQ ID NO: 8)
    si6: AGGUGGAUGGAAAGCAGGUAGAGUU (SEQ ID NO: 9)
    si7: CAGGUAGAGUUGGCUUUGUGGGACA (SEQ ID NO: 10)
    si8: ACCCAGAUACCGAUGUUAUACUGAU (SEQ ID NO: 11)
    si9: CCAGAUACCGAUGUUAUACUGAUGU (SEQ ID NO: 12)
    si10: GAUACCGAUGUUAUACUGAUGUGUU
```

Therapeutic Agent Comprising DNA Utilized for Zinc Finger Nuclease Technology

Zinc finger nuclease technology is a technology using a restriction enzyme, which is a chimeric nuclease comprising a zinc finger DNA recognition domain and a DNA cleavage domain for recognition and cleavage of various DNA sequences. Zinc finger nucleases can induce targeted double strand break from genomic DNA when the nucleases are transferred into cells. Zinc finger nucleases, therefore, can be used to cause an efficient gene mutation in cells comprising a polynucleotide of interest. When double strand break occurs in a cell, the cell repairs the cleaved site using a repair system of the cell itself. When donor DNA with DNA sequence similar to the cleaved site is transferred into the cells during the repair, homologous recombination occurs between the cleaved DNA and the donor DNA. This causes a desired mutation at a particular site on a gene comprising the sequence of donor DNA. On the other hand, even if the cells do not comprise donor DNA, cells comprising cleaved DNA as described above can repair the cleaved sites by non-homologous end joining. In the non-homologous end joining, two cleaved ends are connected together to repair the cleaved DNA without resulting in a mutation in general. In some cases, however, the repair may cause errors such as insertion or deletion of base pair at the ends of the cleaved DNA. Accordingly, when zinc finger nucleases are used to result in double strand break at particular sites of base sequence and induce non-homologous end joining, mutation can be caused in the DNA and thus knockout cell lines can be produced (Urnov et al. (Nature (2005) 435 (7042) 646), Lombardo et al. (Nat. Biotechnol. (2007) 25 (11) 1298), Do et al. (Mutat. Res. (2012) 740 (1-2) 34).

6. Therapeutic Agent for Cancer

In a non-limiting aspect, the present invention relates to a therapeutic agent for cancer that comprises, as an active ingredient, a polynucleotide or a recombinant vector according to the present invention, or a compound selected by a screening method of the present invention and that is based on inhibition or antagonization of the function of the RHOA mutant polypeptide and/or the expression of the RHOA mutant polypeptide. The therapeutic agent according to the present invention can be a medicament comprising, as an active ingredient, an effective amount of at least one of the polynucleotide, the recombinant vector, or the compound according to the present invention. Generally, therapeutic agents are desirably prepared with one or more than one pharmaceutically acceptable carrier (pharmaceutical carrier).

Patients with cancer having the RHOA mutant polypeptide of the present invention can be selected for subjects to whom the therapeutic agent of the present invention is administered. In other words, any cancer may be selected for a therapeutic target as long as the cancer has the RHOA mutant polypeptide of the present invention. Suitable non-limiting aspects of the cancer having the RHOA mutant polypeptide of the present invention can include gastric cancer, colorectal cancer, breast cancer, and lung cancer.

The amount of the active ingredient contained in the therapeutic agent for cancer according to the present invention is appropriately selected from a wide range of amounts. A dose for any patient will depend on many factors including size, body surface area, and age of the patient, a particular therapeutic agent to be administered, sex, duration and route of administration, systemic health, and other drugs to be administered simultaneously. Generally, the dose appropriately ranges from, but is not limited to, about 0.00001 to 70% by weight, preferably about 0.0001 to 5% by weight. If a polynucleotide such as siRNA is used as an active ingredient, the dose can be represented using as a unit the copy number of the polynucleotide molecule in addition to % by weight as described above. A dose of the polynucleotide molecule for intravenous administration can be selected from about $10^6$ to $10^{22}$ copies of the nucleic acid molecule.

Examples of the pharmaceutical carrier can include diluents and excipients such as fillers, extenders, binders, humectants, disintegrating agents, and lubricating agents commonly used depending on usage of the therapeutic agent. These pharmaceutical carriers can be appropriately selected and used according to usage of the resultant therapeutic agent. These pharmaceutical carriers include for example water, pharmaceutically acceptable organic solvents, collagen, polyvinyl alcohols, polyvinyl pyrrolidone, carboxyvinyl polymers, sodium alginate, water soluble dextrans, sodium carboxymethyl starch, pectin, xanthan gum, gum arabic, casein, gelatin, agar, glycerin, propylene glycol, polyethylene glycol, vaseline, paraffin, stearyl alcohol, stearic acid, human serum albumin, mannitol, sorbitol, and lactose. These pharmaceutical carriers can be appropriately used in combination with one or more than one pharmaceutical carrier according to usage of the therapeutic agent according to the present invention.

The therapeutic agent of the present invention can be prepared, if desired, with various ingredients used in common formulations, for example, a stabilizing agent, a germicide, a buffering agent, an isotonizing agent, a chelating agent, a pH adjusting agent, and a surfactant.

Examples of the stabilizing agent can include human serum albumin, common L-amino acids, sugars, and cellulosic derivatives, which can be used alone or in combination with, for example, surfactants. Especially, this combination can increase stability of active ingredients. The L-amino acids are especially not limited but may be for example glycine, cysteine, or glutamic acid. The sugars are also especially not limited but may be for example monosaccharides such as glucose, mannose, galactose, and fructose, sugar alcohols such as mannitol, inositol, and xylitol, disaccharides such as sucrose, maltose, and lactose, polysaccharides such as dextran, hydroxypropyl starch, chondroitin sulfate, and hyaluronic acid, or derivatives thereof. The cellulosic derivatives are also especially not limited but may be methyl cellulose, ethyl cellulose, hydroxyethyl cellulose, hydroxypropyl cellulose, hydroxypropyl methylcellulose, or sodium carboxymethyl cellulose.

The surfactants are also especially not limited but either ionic or nonionic surfactant can be used. These surfactants include, for example, polyoxyethylene glycol sorbitan alkyl esters, polyoxyethylene alkyl ethers, sorbitan monoacyl esters, and fatty acid glycerides.

Examples of the buffering agent can include boric acid, phosphoric acid, acetic acid, citric acid, ε-aminocaproic acid, glutamic acid, and/or salts thereof (such as alkaline metal salts and alkaline-earth metal salts including sodium, potassium, calcium, and magnesium salts).

Examples of the isotonizing agent can include sodium chloride, potassium chloride, sugars, and glycerin.

Examples of the chelating agent can include sodium edetate and citric acid.

The therapeutic agent according to the present invention can be used in the form of a liquid formulation. Alternatively, the therapeutic agent can be used in the form of a formulation that is prepared by lyophilizing the liquid formulation to obtain a lyophilizate that can be stored, dissolving the lyophilizate in water or a buffer including physiological saline at the time of use, and adjusting its concentration appropriately.

siRNA therapies are performed by using a standard vector to which a polynucleotide comprising siRNA of the present invention is inserted and/or by using a gene delivery system delivering a polynucleotide including synthetic siRNA to administer the polynucleotide to a patient. Typically, siRNA of the present invention is chemically stabilized to avoid nuclease degradation in vivo. Methods of preparing chemically stabilized RNA molecules are known in the art. For example, the molecules may have a modified scaffold and nucleotide to avoid ribonuclease action. Other modifications are also available (Song et al. (Nature Med. (2003) 9, 347)). Suitable polynucleotide delivery systems can include a liposome, a receptor-mediated delivery system, and a viral vector such as herpesvirus, retrovirus, adenovirus, and adeno-associated virus among others. The vector may have gene information required for expression in target cells, for example promoter. The therapeutic agent of the present invention can also include gene delivery systems as described above.

The therapeutic agent of the present invention can be administered via an administration route including oral administration and parenteral administration such as intravenous, sub-cutaneous, intra-muscular, and intraperitoneal route.

It is noted that all related art documents cited herein are incorporated herein by reference.

The present invention will be now described more specifically in the Examples below but is not limited to the Examples.

EXAMPLES

Example 1: Detection of RHOA Mutations

OCT-embedded frozen tissues from 30 cases of histologically scirrhous anaplastic adenocarcinoma were sliced to obtain sections of cancer and non-cancer sites. The sections were prepared using a cryostat (Leica, CM1850). Exons contained in 1 μg of DNA extracted from the sections using QIAamp DNA Mini Kit (QIAGEN) were captured using SureSelect Human All Exon Kit (Agilent). All exomes were analyzed by Hiseq 2000 (Illumina) (100b paired end). Average depth was 99× in the cancer sites and 102× in the non-cancer sites. Non synonymous mutations among somatic mutations were listed in order of frequency and 7/30 (21%) of recurrent mutations were found in RHOA gene. The 7 cases of mutations included 1 case of R5W, 1 case of L22R, 4 cases of Y42C, and 1 case of Y74D.

Fifty-seven cases of similar frozen tissue specimens were newly added and in a total of 87 cases, targeted sequencing of RHOA gene was performed. Primers for amplicon sequencing that targets exon regions of RHOA gene were designed by Design Studio, an application provided by Illumina, Inc. (wherein the amplicon size is 175 b). A library was prepared from 250 ng of DNA using a customized TruSeq Custom Amplicon Kit and sequenced by rapid run mode of HiSeq2500 from Illumina, Inc. (150b paired end). Average depth was 4152× in the cancer sites and 3924× in the non-cancer sites. In 22/87 (25%) of cases, somatic mutations were observed in RHOA gene. The 22 cases of mutations included 4 cases of R5W, 1 case of R5Q, 1 case of mutation R5W/R68P, 3 cases of G17E, 1 case of L22R, 1 case of V38G, 6 cases of Y42C, 1 case of E54K, 1 case of W58S, 2 cases of L69R, and 1 case of Y74D.

Example 2: Search for RHOA Mutant Cell Lines

RHOA mutations were analyzed in cancer cell lines of gastric cancer, colorectal cancer, breast cancer, and lung squamous carcinoma. Exon 2 and exon 3 comprising amino acid mutations detected in clinical specimens were amplified by PCR using DNA extracted from cancer cells using DNeasy Blood & Tissue Kit (QIAGEN). The presence or absence of the mutation in the amplified PCR fragments was analyzed using BigDye® Terminator v3.1 Cycle Sequencing Kit (Applied Biosystems) and 3730 DNA Analyzer (Applied Biosystems). The sequences of the primers used in the PCR are shown in Table 1.

TABLE 1

The sequences of the primers used in the amplification of exon 2 and exon 3

| | |
|---|---|
| Exon 2 forward | GTTTTGTGTTTCAGCAATGG (SEQ ID NO: 13) |
| Exon 2 reverse | GTATACTCACCTGCTTTCCATCC (SEQ ID NO: 14) |
| Exon 3 forward | TTCCCATTACAGGTAGAGTTG (SEQ ID NO: 15) |
| Exon 3 reverse | AGGGCCACTCACCTAAACTATC (SEQ ID NO: 16) |

The analysis concludes that the Y42S mutation was present in gastric cardia cancer cell line OE19, that the G17E mutation was present in colorectal cancer cell line SW948 and breast cancer line BT474, and that the G17A mutation was present in lung squamous carcinoma cell line HCC95 (FIG. 1). In contrast, no RHOA mutation was detected in gastric cancer cell line AGS and breast cancer cell line HCC38.

Example 3: Inhibition of Cell Growth by siRNAs Targeting RHOA with Cancer Cell Lines Having Mutations at Positions G17 and Y42 of RHOA and Cancer Cell Lines with Wild Type RHOA Loss of expression of RHOA by siRNAs targeting RHOA and following inhibition of cell growth were investigated in OE19 having the Y42S mutation, in SW948 and BT474 having the G17E mutation, in HCC95 having the: G17A mutation, wherein the mutations are present in RHOA, and in AGS and HCC38 having wild type RHOA. Two siRNA constructs (Life Technologies) were used as RHOA targeting siRNAs. Silencer® Select Negative Control #1 siRNA (Life Technologies) construct was used as a negative control. KIF11-siRNA (Life Technologies) construct was used as a positive control. The sequences used in RHOA and KIF11 siRNA constructs are shown in Table 2.

TABLE 2

Sequences of RHOA and KIF11 siRNAs

| | |
|---|---|
| KIF11 siRNA sense | CCAUCAACACUGGUAAGAAUU (SEQ ID NO: 17) |
| KIF11 siRNA antisense | UUCUUACCAGUGUUGAUGGGU (SEQ ID NO: 18) |
| RHOA siRNA #2 sense | CUAUGAUUAUUAACGAUGUUU (SEQ ID NO: 19) |
| RHOA siRNA #2 antisense | ACAUCGUUAAUAAUCAUAGUU (SEQ ID NO: 20) |
| RHOA siRNA #3 sense | GGCUUUACUCCGUAACAGAUU (SEQ ID NO: 21) |
| RHOA siRNA #3 antisense | UCUGUUACGGAGUAAAGCCCU (SEQ ID NO: 22) |

The above-mentioned cell lines were seeded in Ultra-Low Attachment Surface plates (Corning). The cells seeded at the density of 1E5 cells/mL in a 96-well plate in 100 μL per well were used to evaluate growth inhibitory activity. The cells seeded at the same density in a 6-well plate in 2.5 mL per well were used to evaluate inhibitory efficiency of mRNA expression by siRNAs. After culturing the cells in an incubator at 37° C. for 2 days, RNA extracted from the cells seeded in a 6-well plate using RNeasy Mini Kit (QIAGEN). Real time PCR was performed using Power SYBR® Green PCR Master Mix (Applied Biosystems), StepOnePlus™ Real-Time PCR Systems (Applied Biosystems), to quantify mRNA. The inhibitory efficiency of RHOA mRNA expression was calculated by using values corrected against the quantitative value of RPS18 measured as an internal standard and considering the value in cells treated with negative control siRNA as 0%. After culturing the cells in an incubator at 37° C. for 7 days after seeding, cell growth inhibitory activity was calculated by using the number of living cells among the cells seeded in a 96-well plate as counted using CellTiter-Glo™ Luminescent Cell Viability Assay (Promega) and considering the value in cells treated with negative control siRNA as 0%. The sequences of the PCR primers used in the real time PCR are shown in Table 3.

TABLE 3

Sequences of primers for real time PCR of RHOA

| | |
|---|---|
| Forward | GGGAGCTAGCCAAGATGAAG (SEQ ID NO: 23) |
| Reverse | GTACCCAAAAGCGCCAATC (SEQ ID NO: 24) |

Figure 2:
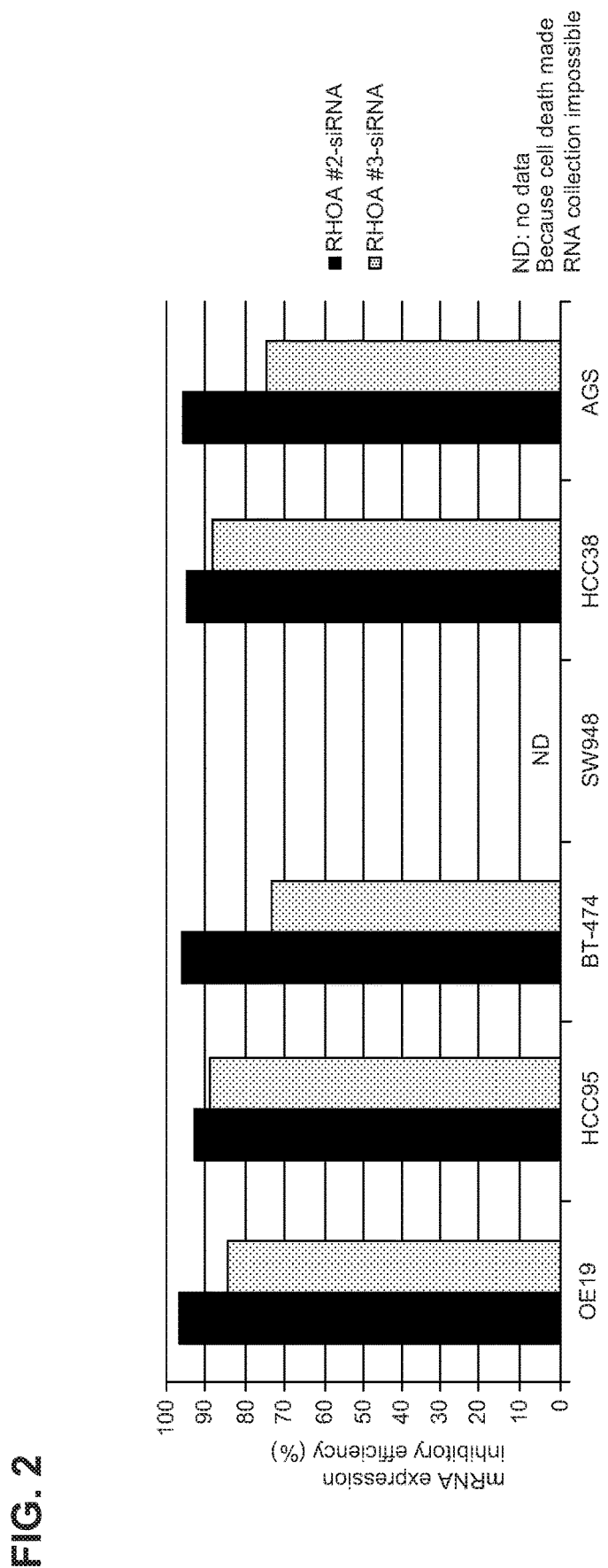
FIG. 2 shows inhibitory efficiency of RHOA mRNA expression by RHOA-siRNA in each cell line.
Figure 3A:
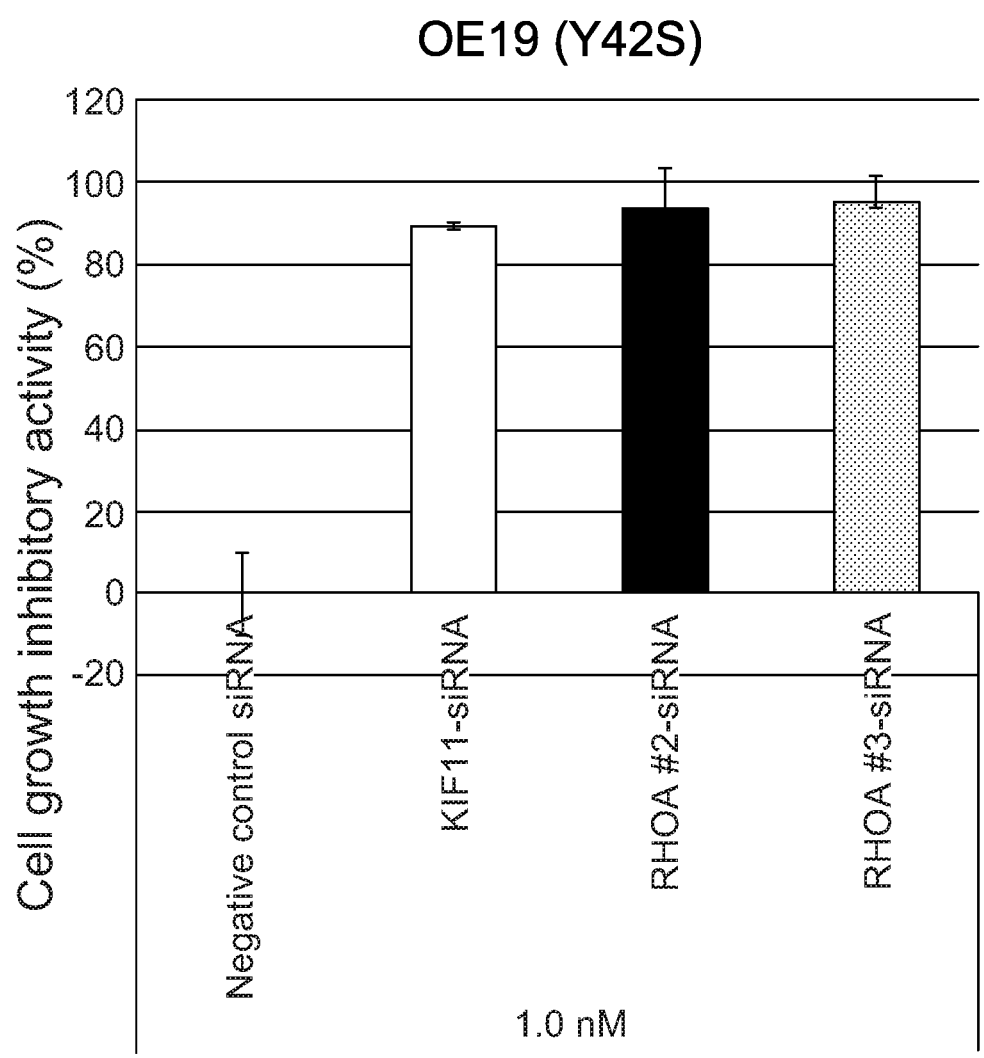
FIG. 3A depicts cell growth inhibitory activity of RHOA-siRNA in OE19 cells having mutation Y42S.
Figure 3B:
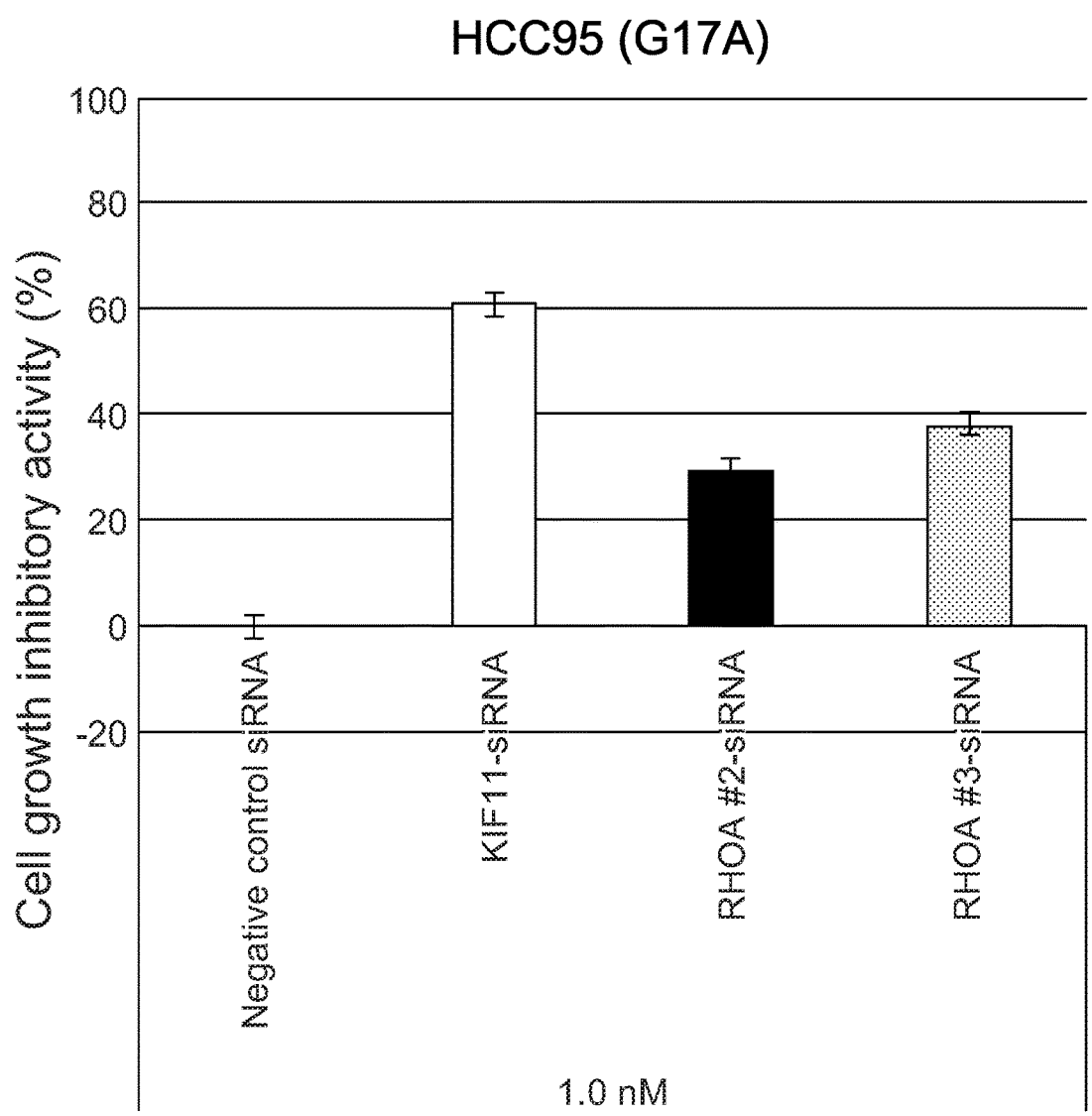
FIG. 3B depicts cell growth inhibitory activity of RHOA-siRNA in HCC95 cells having mutation G17A.
Figure 3C:
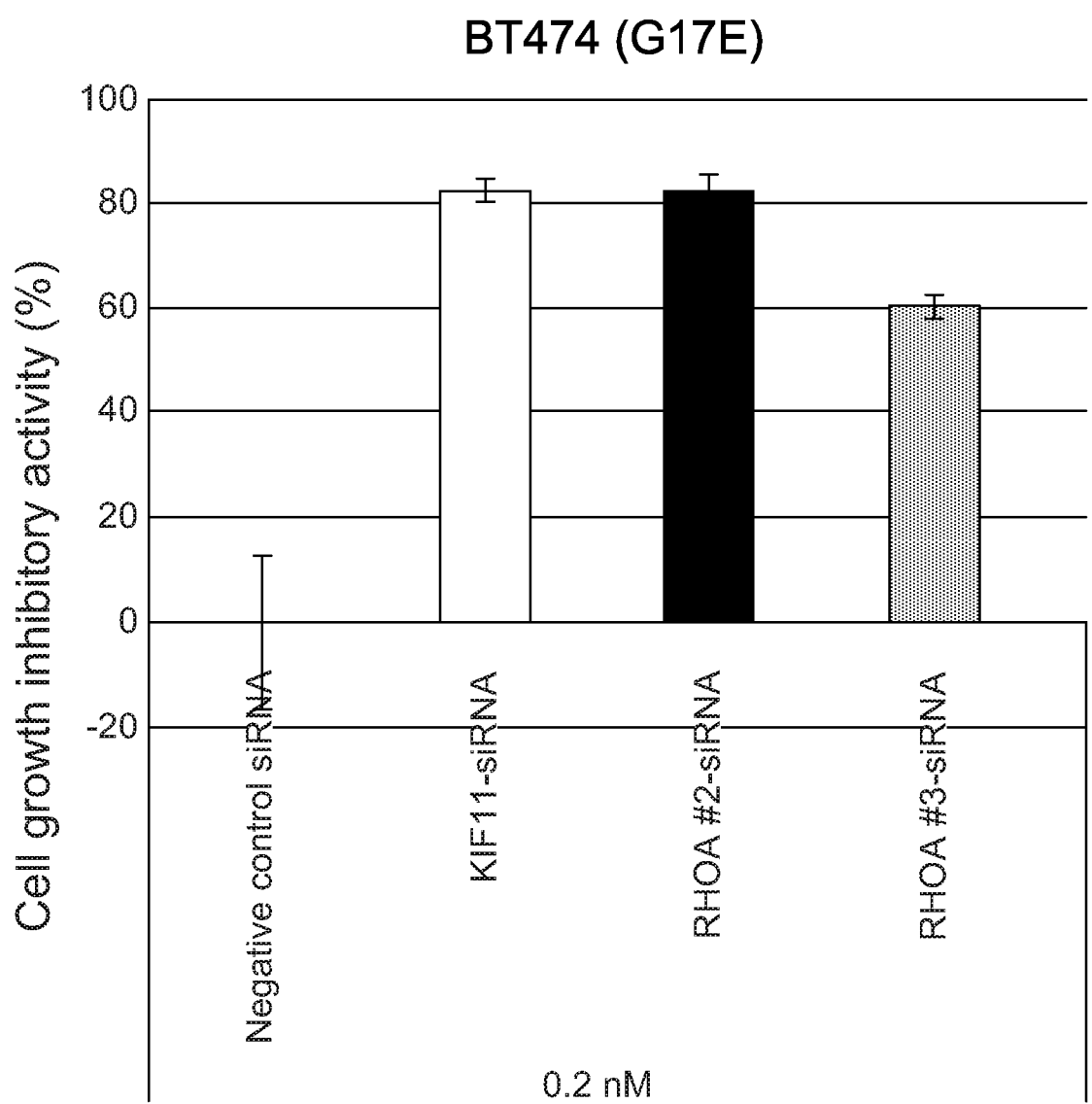
FIG. 3C depicts cell growth inhibitory activity of RHOA-siRNA in SW948 cells having mutation G17E.
Figure 3D:
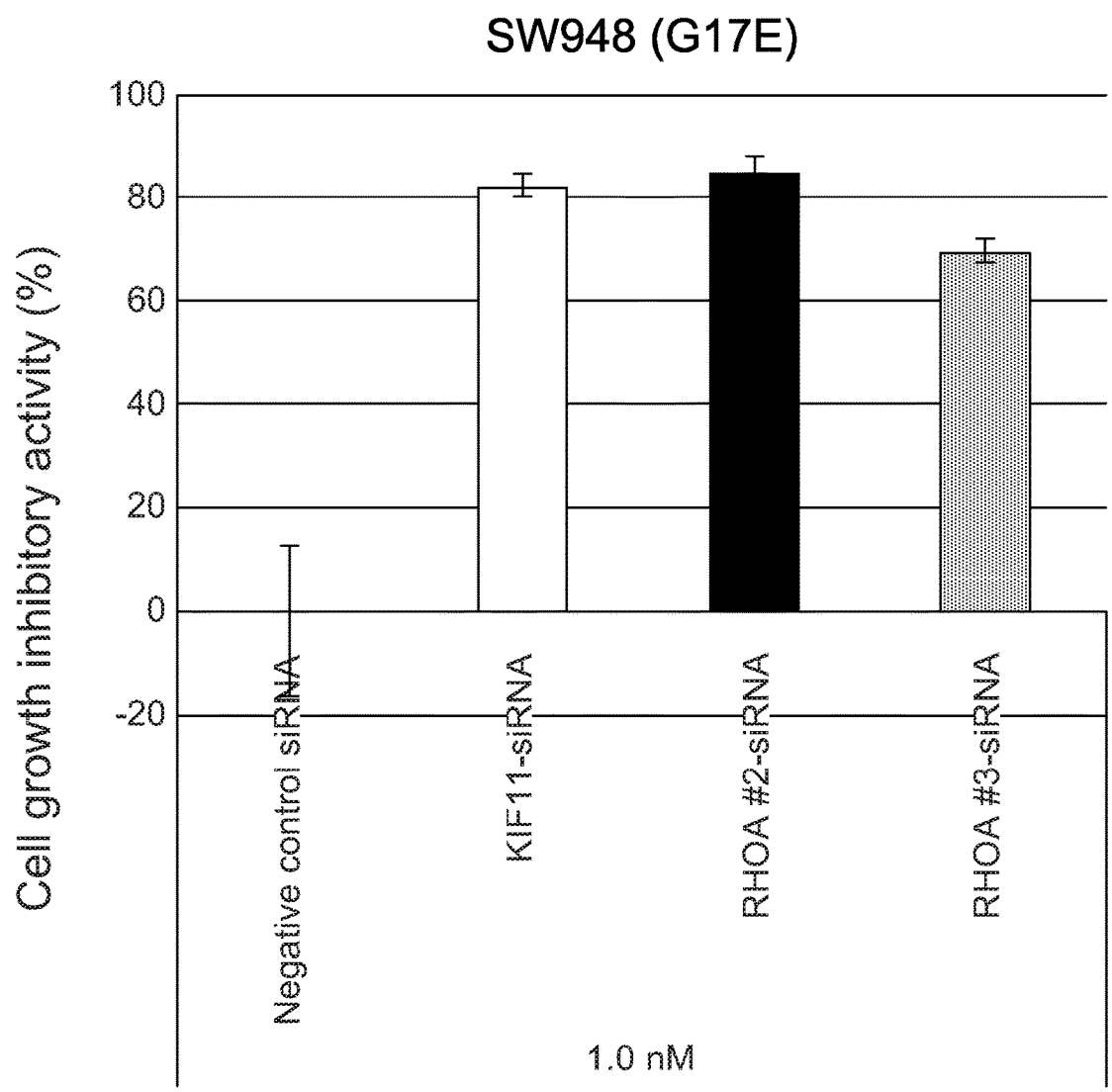
FIG. 3D depicts cell growth inhibitory activity of RHOA-siRNA in BT474 cell having mutation G17E.
Figure 3E:
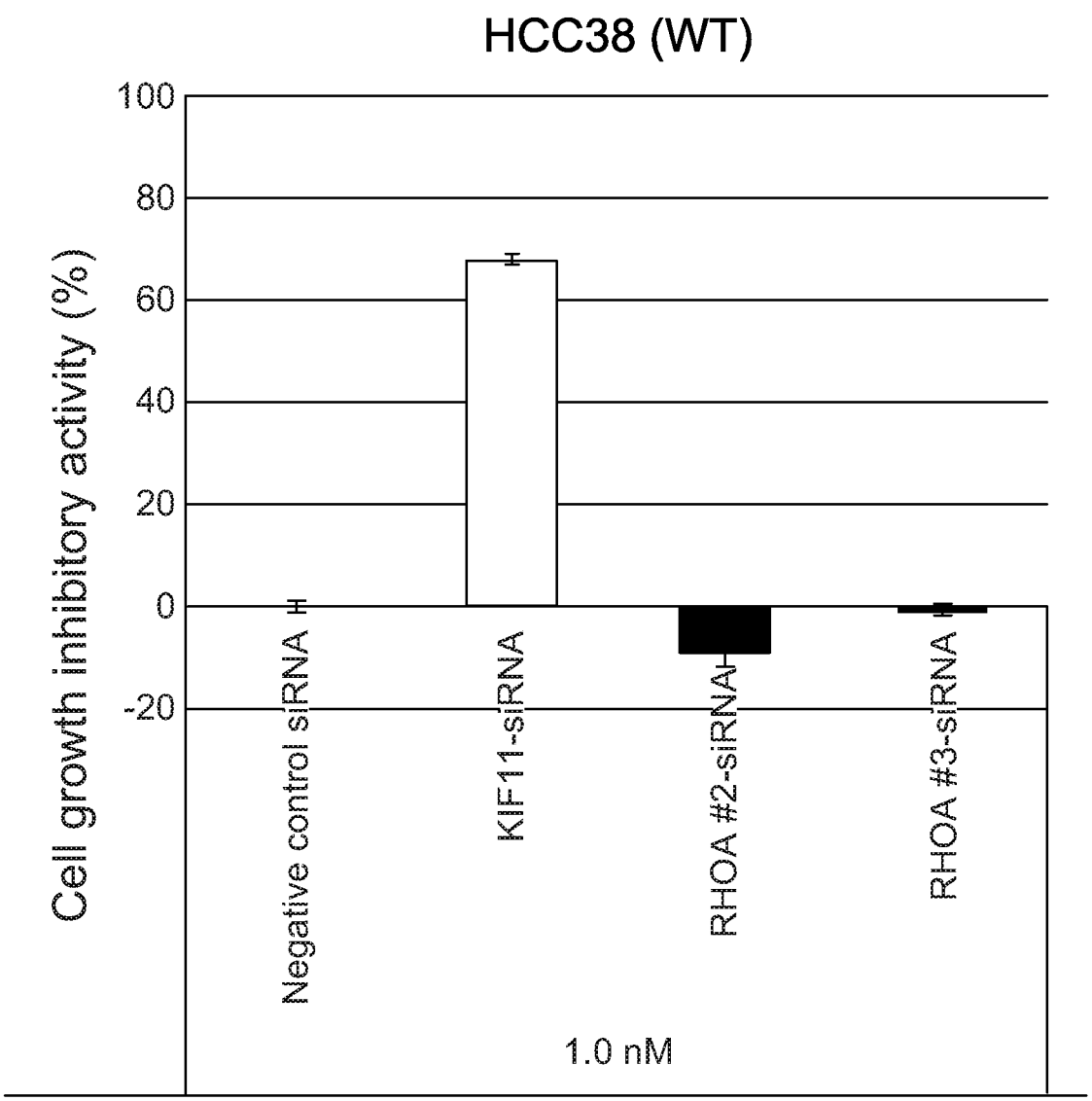
FIG. 3E depicts cell growth inhibitory activity of RHOA-siRNA in HCC38 cell having wild type RHOA.
Figure 3F:
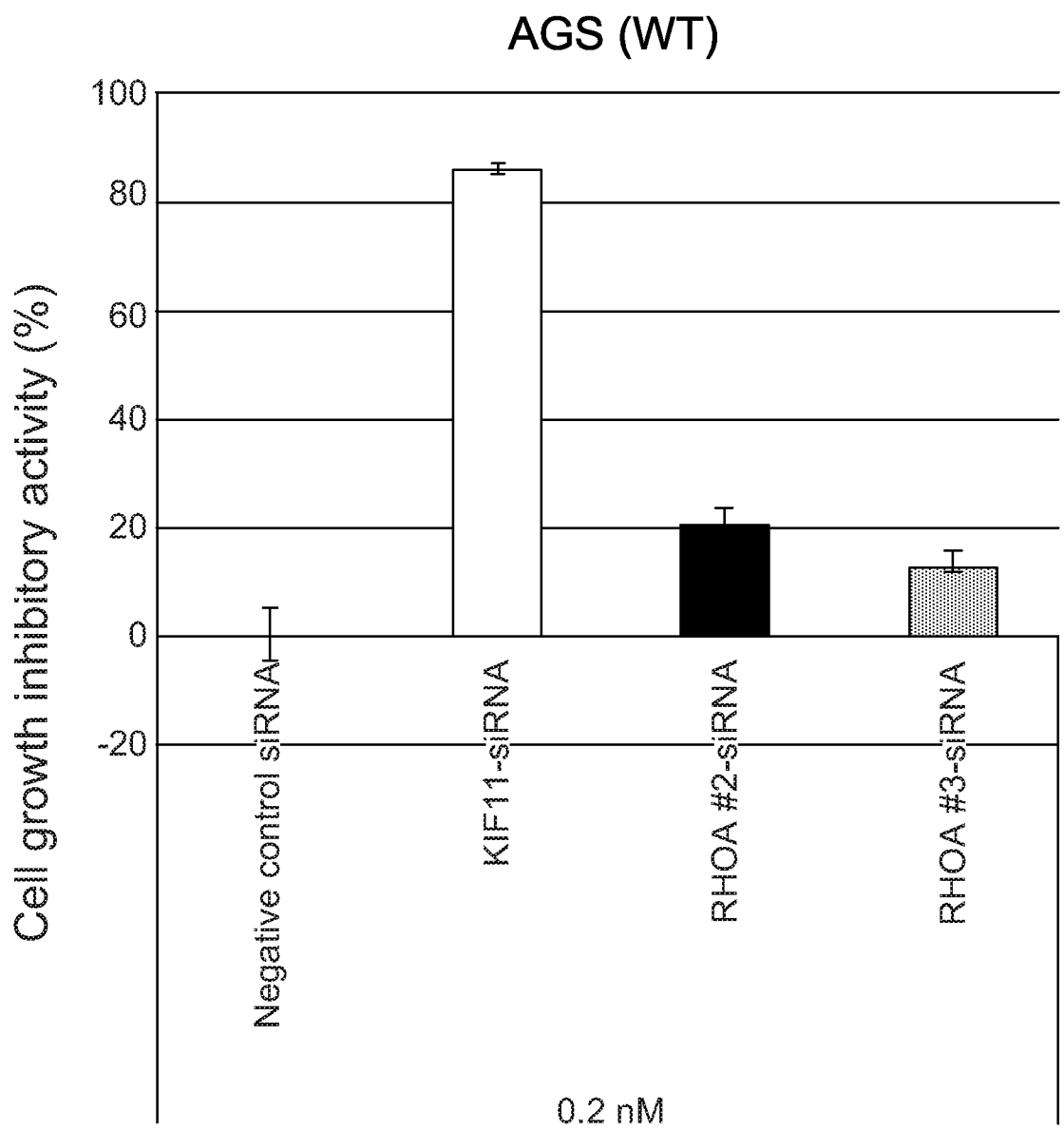
FIG. 3F depicts cell growth inhibitory activity of RHOA-siRNA in AGS cell having wild type RHOA.

Both RHOA siRNAs #2 and #3 showed inhibitory efficiencies of 85 to 99% of RHOA mRNA expression in the evaluated cell lines (FIG. 2).

Cell growth in OE19 having the Y42S mutation and in SW948 and BT474 having the G17E mutation was very strongly inhibited by RHOA siRNAs #2 and #3 by equal to or more than the cell growth in positive control. Cell growth in HCC95 having the G17A mutation was also inhibited. In contrast, cell growth in HCC38 and AGS having wild type RHOA was hardly inhibited by RHOA siRNAs #2 and #3 (FIG. 3).

Example 4: Comparison of RHOA mRNA Levels in Various Cancer Cell Lines and Normal Tissues RHOA has been reported to be highly expressed in cancer in some papers (Non Patent Literatures 6-8). Thus, expression levels of RHOA were compared in cancer cell lines and normal tissues. RNA from normal large intestine tissue and normal lung tissue, RNA from normal stomach, and RNA from normal breast, which were respectively purchased from Ambion, Stratagene, and Clontech, were used. These RNAs were used as templates to perform real time PCR using Power SYBR® Green PCR Master Mix (Applied Biosystems) and StepOnePlus™ Real-Time PCR Systems (Applied Biosystems) to quantify RHOA mRNA. RHOA mRNA levels were calculated by using the value corrected against the value of RPS18 measured as an internal standard.

Figure 4:
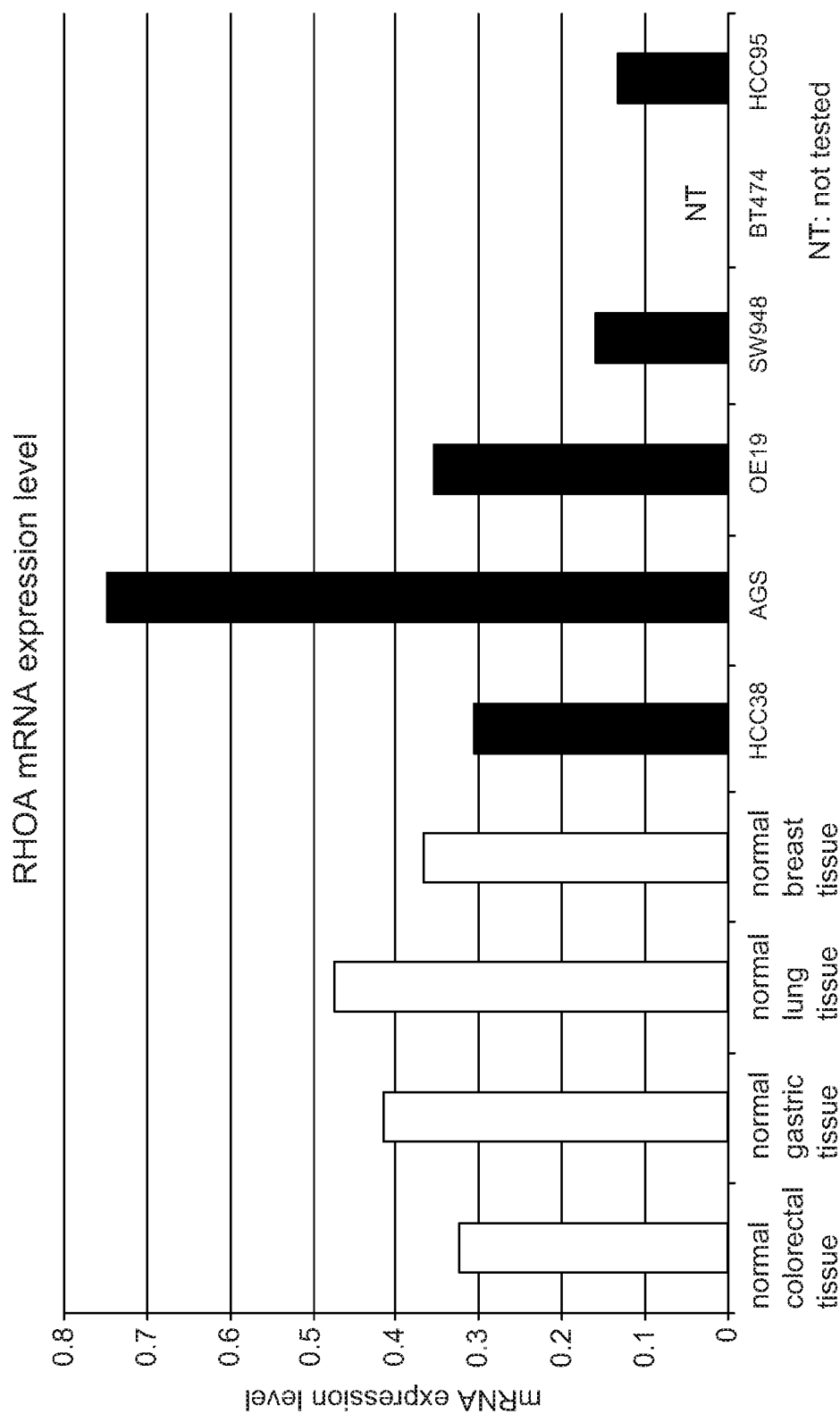
FIG. 4 depicts RHOA expression levels in normal large intestine, lung, gastric, and breast tissues and OE19, SW948, BT474, HCC95, HCC38, and AGS.

RHOA expression levels equal to or less than those in normal tissues were shown in the evaluated cell lines (see FIG. 4). When RHOA expression levels in OE19, SW948, BT474, and HCC95 in which cell growth was inhibited by RHOA siRNAs were compared with RHOA expression levels in HCC38 and AGS in which cell growth was not inhibited by RHOA siRNAs, no correlation was observed between the cell growth inhibitory activity and the expression level.

What is claimed is:

1. A vector comprising a polynucleotide encoding a polypeptide having a mutation in the amino acid sequence set forth in SEQ ID NO:1, wherein the mutation is at an amino acid residue position selected from the group consisting of
   a substitution of Arg at position 5 by Trp,
   a substitution of Gly at position 17 by Glu,
   Leu at position 22,
   Glu at position 54, and
   Tyr at position 74.

2. The vector according to claim 1, wherein the polynucleotide encodes a polypeptide having a mutation in the amino acid sequence set forth in SEQ ID NO:1 selected from the group consisting of
   Arg at position 5 is substituted by Trp;
   Gly at position 17 is substituted by Glu;
   Leu at position 22 is substituted by Arg;
   Glu at position 54 is substituted by Lys; and
   Tyr at position 74 is substituted by Asp.

3. A cell comprising the vector according to claim 1.

4. A cell comprising the vector according to claim 2.

5. A method of screening therapeutic agents for cancer, comprising
   contacting a test substance with a cell that comprises a vector comprising a polynucleotide encoding a polypeptide having a mutation in the amino acid sequence set forth in SEQ ID NO:1, wherein the mutation is at an amino acid residue position selected from the group consisting of
   Arg at position 5,
   Gly at position 17,
   Leu at position 22,
   Tyr at position 42,
   Glu at position 54, and
   Tyr at position 74, and
   selecting a compound having the ability to knock down the expression of the polynucleotide encoding the polypeptide having the mutation as a candidate therapeutic agent for cancer.

6. The method according to claim 5, which further comprises the step of contacting the test substance with a cell of a cancer cell line that contains a polynucleotide encoding a polypeptide having the mutation in the amino acid sequence set forth in SEQ ID NO:1 and
   measuring the expression of the polynucleotide encoding the polypeptide having the mutation.

7. The method according to claim 6 wherein the cell line is from a gastric cancer, colorectal cancer, breast cancer, or lung cancer.

8. A method of screening therapeutic agents for cancer, comprising
   contacting a test substance with a cell that comprises a vector comprising a polynucleotide encoding a polypeptide having a mutation in the amino acid sequence set forth in SEQ ID NO:1, wherein the mutation is at an amino acid residue position selected from the group consisting of
   Arg at position 5,
   Gly at position 17,
   Leu at position 22,
   Tyr at position 42,
   Glu at position 54, and
   Tyr at position 74,
   monitoring cell growth of the contacted cell, and
   selecting a compound having the ability to inhibit cell growth of the contacted cell as a candidate therapeutic agent for cancer.

9. The method according to claim 8, which further comprises the step of contacting the test substance with a cell of a cancer cell line that contains a polynucleotide encoding a polypeptide having the mutation in the amino acid sequence set forth in SEQ ID NO:1, and
   monitoring cell growth of the contacted cell.

10. A method of screening a sample of gastric cancer, colorectal cancer, breast cancer, or lung cancer for the presence of a polynucleotide encoding a mutant polypeptide, comprising contacting said sample with a primer that hybridizes to a polynucleotide encoding a mutation in the amino acid sequence set forth in SEQ ID NO:1, wherein the mutation selected from the group consisting of
   a substitution of Arg at position 5 by Trp,
   a substitution of Gly at position 17 by Glu,
   Leu at position 22,
   Tyr at position 42,
   Glu at position 54, and
   Tyr at position 74,
   wherein the primer does not hybridize to a polynucleotide encoding the amino acid sequence set forth in SEQ ID NO:1, and
   detecting the presence of a hybridization product using a polymerase chain reaction (PCR) method, wherein the presence of a hybridization product indicates the presence of a polynucleotide encoding the mutant polypeptide.

11. The method according to claim 10, wherein the encoded mutant polypeptide contains a mutation in the amino acid sequence set forth in SEQ ID NO:1 selected from the group consisting of
   a substitution of Arg at position 5 by Trp,
   a substitution of Gly at position 17 by Glu,
   a substitution of Leu at position 22 by Arg,
   a substitution of Tyr at position 42 by Cys,
   a substitution of Glu at position 54 by Lys, and
   a substitution of Tyr at position 74 by Asp.

12. An siRNA that comprises a sense strand comprising the nucleotide sequence of SEQ ID NO:19 and an antisense strand consisting of SEQ ID NO:20; or a sense strand comprising the nucleotide sequence of SEQ ID NO:21 and an antisense strand consisting of SEQ ID NO:22.

\* \* \* \* \*

SEQUENCE LISTING

<160> NUMBER OF SEQ ID NOS: 35

<210> SEQ ID NO 1
<211> LENGTH: 193
<212> TYPE: PRT
<213> ORGANISM: Homo sapiens

<400> SEQUENCE: 1

```
Met Ala Ala Ile Arg Lys Lys Leu Val Ile Val Gly Asp Gly Ala Cys
1               5                   10                  15

Gly Lys Thr Cys Leu Leu Ile Val Phe Ser Lys Asp Gln Phe Pro Glu
            20                  25                  30

Val Tyr Val Pro Thr Val Phe Glu Asn Tyr Val Ala Asp Ile Glu Val
        35                  40                  45

Asp Gly Lys Gln Val Glu Leu Ala Leu Trp Asp Thr Ala Gly Gln Glu
    50                  55                  60

Asp Tyr Asp Arg Leu Arg Pro Leu Ser Tyr Pro Asp Thr Asp Val Ile
65                  70                  75                  80

Leu Met Cys Phe Ser Ile Asp Ser Pro Asp Ser Leu Glu Asn Ile Pro
                85                  90                  95

Glu Lys Trp Thr Pro Glu Val Lys His Phe Cys Pro Asn Val Pro Ile
            100                 105                 110

Ile Leu Val Gly Asn Lys Lys Asp Leu Arg Asn Asp Glu His Thr Arg
        115                 120                 125

Arg Glu Leu Ala Lys Met Lys Gln Glu Pro Val Lys Pro Glu Glu Gly
    130                 135                 140

Arg Asp Met Ala Asn Arg Ile Gly Ala Phe Gly Tyr Met Glu Cys Ser
145                 150                 155                 160

Ala Lys Thr Lys Asp Gly Val Arg Glu Val Phe Glu Met Ala Thr Arg
                165                 170                 175

Ala Ala Leu Gln Ala Arg Arg Gly Lys Lys Ser Gly Cys Leu Val
            180                 185                 190

Leu
```

<210> SEQ ID NO 2
<211> LENGTH: 1926
<212> TYPE: DNA
<213> ORGANISM: Homo sapiens

<400> SEQUENCE: 2

```
gtggatgagc tgtgagtgcg cgcgcgtgcg cggggccgcg acctgtgccg gctcgagccc      60
gctgggcact cggaggcgcg cacgtcgttc cccgccctcc cgccgccgcc cgccctcgct     120
ctctcgcgct accctcccgc cgcccgcggt cctccgtcgg ttctctcgtt agtccacggt     180
ctggtcttca gctacccgcc ttcgtctccg agtttgcgac tcgcggaccg gcgtccccgg     240
cgcgaagagg ctggactcgg attcgttgcc tgagcaatgg ctgccatccg gaagaaactg     300
gtgattgttg gtgatggagc ctgtggaaag acatgcttgc tcatagtctt cagcaaggac     360
cagttcccag aggtgtatgt gcccacagtg tttgagaact atgtggcaga tatcgaggtg     420
gatggaaagc aggtagagtt ggctttgtgg gacacagctg gcaggaaga ttatgatcgc      480
ctgaggcccc tctcctaccc agataccgat gttatactga tgtgttttc catcgacagc      540
cctgatagtt tagaaaacat cccagaaaag tggaccccag aagtcaagca tttctgtccc     600
aacgtgccca tcatcctggt tgggaataag aaggatcttc ggaatgatga gcacacaagg     660
cgggagctag ccaagatgaa gcaggagccg gtgaaacctg aagaaggcag agatatggca     720
aacaggattg gcgcttttgg gtacatggag tgttcagcaa agaccaaaga tggagtgaga     780
gaggtttttg aaatggctac gagagctgct ctgcaagcta gacgtgggaa gaaaaaatct     840
gggtgccttg tcttgtgaaa ccttgctgca agcacagccc ttatgcggtt aattttgaag     900
tgctgtttat taatcttagt gtatgattac tggccttttt catttatcta aatttaccct     960
aagattacaa atcagaagtc atcttgctac cagtatttag aagccaacta tgattattaa    1020
cgatgtccaa cccgtctggc ccaccagggt ccttttgaca ctgctctaac agccctcctc    1080
tgcactccca cctgacacac caggcgctaa ttcaggaat ttcttaactt cttgcttctt     1140
tctagaaaga gaaacagttg gtaacttttg tgaattaggc tgtaactact ttataactaa    1200
catgtcctgc ctattatctg tcagctgcaa ggtactctgg tgagtcacca cttcagggct    1260
ttactccgta acagattttg ttggcatagc tctggggtgg gcagtttttt gaaaatgggc    1320
tcaaccagaa aagcccaagt tcatgcagct gtggcagagt tacagttctg tggtttcatg    1380
ttagttacct tatagttact gtgtaattag tgccacttaa tgtatgttac caaaaataaa    1440
tatatctacc ccagactaga tgtagtattt tttgtataat tggatttcct aatactgtca    1500
tcctcaaaga aagtgtattg gtttttttaaa aaagaaagtg tatttggaaa taagtcaga    1560
tggaaaattc atttttttaaa ttcccgtttt gtcacttttt ctgataaaag atggccatat    1620
tacccctttt cggccccatg tatctcagta ccccatggag ctgggctaag taaataggaa    1680
ttggtttcac gcctgaggca attagacact ttggaagatg gcataacctg tctcacctgg    1740
acttaagcat ctggctctaa ttcacagtgc tcttttctcc tcactgtatc caggttccct    1800
cccagaggag ccaccagttc tcatgggtgg cactcagtct ctcttctctc cagctgacta    1860
aactttttt ctgtaccagt taattttcc aactactaat agaataaagg cagttttcta     1920
aaaaaa                                                              1926
```

<210> SEQ ID NO 3
<211> LENGTH: 25
<212> TYPE: RNA
<213> ORGANISM: Artificial Sequence
<220> FEATURE:
<223> OTHER INFORMATION: si1

<400> SEQUENCE: 3

```
gaaagacaug cuugcucaua gucuu                                           25
```

```
<210> SEQ ID NO 4
<211> LENGTH: 25
<212> TYPE: RNA
<213> ORGANISM: Artificial Sequence
<220> FEATURE:
<223> OTHER INFORMATION: si2

<400> SEQUENCE: 4
cagaggugua ugugcccaca guguu                                              25

<210> SEQ ID NO 5
<211> LENGTH: 25
<212> TYPE: RNA
<213> ORGANISM: Artificial Sequence
<220> FEATURE:
<223> OTHER INFORMATION: si3

<400> SEQUENCE: 5
uguuugagaa cuauguggca gauau                                              25

<210> SEQ ID NO 6
<211> LENGTH: 25
<212> TYPE: RNA
<213> ORGANISM: Artificial Sequence
<220> FEATURE:
<223> OTHER INFORMATION: si4

<400> SEQUENCE: 6
uggcagauau cgagguggau ggaaa                                              25

<210> SEQ ID NO 7
<211> LENGTH: 25
<212> TYPE: RNA
<213> ORGANISM: Artificial Sequence
<220> FEATURE:
<223> OTHER INFORMATION: si5

<400> SEQUENCE: 7
ucgaggugga uggaaagcag guaga                                              25

<210> SEQ ID NO 8
<211> LENGTH: 25
<212> TYPE: RNA
<213> ORGANISM: Artificial Sequence
<220> FEATURE:
<223> OTHER INFORMATION: si6

<400> SEQUENCE: 8
agguggaugg aaagcaggua gaguu                                              25

<210> SEQ ID NO 9
<211> LENGTH: 25
<212> TYPE: RNA
<213> ORGANISM: Artificial Sequence
<220> FEATURE:
<223> OTHER INFORMATION: si7

<400> SEQUENCE: 9
cagguagagu uggcuuugug ggaca                                              25

<210> SEQ ID NO 10
<211> LENGTH: 25
<212> TYPE: RNA
<213> ORGANISM: Artificial Sequence
<220> FEATURE:
```

```
<223> OTHER INFORMATION: si8

<400> SEQUENCE: 10
acccagauac cgauguuaua cugau                                              25

<210> SEQ ID NO 11
<211> LENGTH: 25
<212> TYPE: RNA
<213> ORGANISM: Artificial Sequence
<220> FEATURE:
<223> OTHER INFORMATION: si9

<400> SEQUENCE: 11
ccagauaccg auguuauacu gaugu                                              25

<210> SEQ ID NO 12
<211> LENGTH: 25
<212> TYPE: RNA
<213> ORGANISM: Artificial Sequence
<220> FEATURE:
<223> OTHER INFORMATION: si10

<400> SEQUENCE: 12
gauaccgaug uuauacugau guguu                                              25

<210> SEQ ID NO 13
<211> LENGTH: 20
<212> TYPE: DNA
<213> ORGANISM: Artificial Sequence
<220> FEATURE:
<223> OTHER INFORMATION: Exon 2 forward

<400> SEQUENCE: 13
gttttgtgtt tcagcaatgg                                                    20

<210> SEQ ID NO 14
<211> LENGTH: 23
<212> TYPE: DNA
<213> ORGANISM: Artificial Sequence
<220> FEATURE:
<223> OTHER INFORMATION: Exon 2 reverse

<400> SEQUENCE: 14
gtatactcac ctgctttcca tcc                                                23

<210> SEQ ID NO 15
<211> LENGTH: 21
<212> TYPE: DNA
<213> ORGANISM: Artificial Sequence
<220> FEATURE:
<223> OTHER INFORMATION: Exon 3 forward

<400> SEQUENCE: 15
ttcccattac aggtagagtt g                                                  21

<210> SEQ ID NO 16
<211> LENGTH: 22
<212> TYPE: DNA
<213> ORGANISM: Artificial Sequence
<220> FEATURE:
<223> OTHER INFORMATION: Exon 3 reverse

<400> SEQUENCE: 16
agggccactc acctaaacta tc                                                 22
```

```
<210> SEQ ID NO 17
<211> LENGTH: 21
<212> TYPE: RNA
<213> ORGANISM: Artificial Sequence
<220> FEATURE:
<223> OTHER INFORMATION: KIF11 siRNA sense

<400> SEQUENCE: 17
ccaucaacac ugguaagaau u                                              21

<210> SEQ ID NO 18
<211> LENGTH: 21
<212> TYPE: RNA
<213> ORGANISM: Artificial Sequence
<220> FEATURE:
<223> OTHER INFORMATION: KIF11 siRNA antisense

<400> SEQUENCE: 18
uucuuaccag uguugaugggg u                                             21

<210> SEQ ID NO 19
<211> LENGTH: 21
<212> TYPE: RNA
<213> ORGANISM: Artificial Sequence
<220> FEATURE:
<223> OTHER INFORMATION: RHOA siRNA #2 sense

<400> SEQUENCE: 19
cuaugauuau uaacgauguu u                                              21

<210> SEQ ID NO 20
<211> LENGTH: 21
<212> TYPE: RNA
<213> ORGANISM: Artificial Sequence
<220> FEATURE:
<223> OTHER INFORMATION: RHOA siRNA #2 antisense

<400> SEQUENCE: 20
acaucguuaa uaaucauagu u                                              21

<210> SEQ ID NO 21
<211> LENGTH: 21
<212> TYPE: RNA
<213> ORGANISM: Artificial Sequence
<220> FEATURE:
<223> OTHER INFORMATION: RHOA siRNA #3 sense

<400> SEQUENCE: 21
ggcuuuacuc cguaacagau u                                              21

<210> SEQ ID NO 22
<211> LENGTH: 21
<212> TYPE: RNA
<213> ORGANISM: Artificial Sequence
<220> FEATURE:
<223> OTHER INFORMATION: RHOA siRNA #3 antisense

<400> SEQUENCE: 22
ucuguuacgg aguaaagccc u                                              21

<210> SEQ ID NO 23
<211> LENGTH: 20
<212> TYPE: DNA
<213> ORGANISM: Artificial Sequence
<220> FEATURE:
<223> OTHER INFORMATION: Forward primer for real-time PCR
```

```
<400> SEQUENCE: 23
gggagctagc caagatgaag                                              20

<210> SEQ ID NO 24
<211> LENGTH: 19
<212> TYPE: DNA
<213> ORGANISM: Artificial Sequence
<220> FEATURE:
<223> OTHER INFORMATION: Reverse primer for real-time PCR

<400> SEQUENCE: 24
gtacccaaaa gcgccaatc                                               19

<210> SEQ ID NO 25
<211> LENGTH: 6
<212> TYPE: PRT
<213> ORGANISM: Artificial Sequence
<220> FEATURE:
<223> OTHER INFORMATION: Peptide variant

<400> SEQUENCE: 25

Thr Val Phe Glu Asn Cys
1               5

<210> SEQ ID NO 26
<211> LENGTH: 6
<212> TYPE: PRT
<213> ORGANISM: Artificial Sequence
<220> FEATURE:
<223> OTHER INFORMATION: Peptide variant

<400> SEQUENCE: 26

Val Phe Glu Asn Cys Val
1               5

<210> SEQ ID NO 27
<211> LENGTH: 6
<212> TYPE: PRT
<213> ORGANISM: Artificial Sequence
<220> FEATURE:
<223> OTHER INFORMATION: Peptide variant

<400> SEQUENCE: 27

Phe Glu Asn Cys Val Ala
1               5

<210> SEQ ID NO 28
<211> LENGTH: 6
<212> TYPE: PRT
<213> ORGANISM: Artificial Sequence
<220> FEATURE:
<223> OTHER INFORMATION: Peptide variant

<400> SEQUENCE: 28

Glu Asn Cys Val Ala Asp
1               5

<210> SEQ ID NO 29
<211> LENGTH: 6
<212> TYPE: PRT
<213> ORGANISM: Artificial Sequence
<220> FEATURE:
<223> OTHER INFORMATION: Peptide variant

<400> SEQUENCE: 29

Asn Cys Val Ala Asp Ile
```

```
1               5

<210> SEQ ID NO 30
<211> LENGTH: 6
<212> TYPE: PRT
<213> ORGANISM: Artificial Sequence
<220> FEATURE:
<223> OTHER INFORMATION: Peptide variant

<400> SEQUENCE: 30

Cys Val Ala Asp Ile Glu
1               5

<210> SEQ ID NO 31
<211> LENGTH: 10
<212> TYPE: PRT
<213> ORGANISM: Artificial Sequence
<220> FEATURE:
<223> OTHER INFORMATION: Peptide variant

<400> SEQUENCE: 31

Val Tyr Val Pro Thr Val Phe Glu Asn Cys
1               5                   10

<210> SEQ ID NO 32
<211> LENGTH: 10
<212> TYPE: PRT
<213> ORGANISM: Artificial Sequence
<220> FEATURE:
<223> OTHER INFORMATION: Peptide variant

<400> SEQUENCE: 32

Tyr Val Pro Thr Val Phe Glu Asn Cys Val
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Peptide variant

<400> SEQUENCE: 33

Val Pro Thr Val Phe Glu Asn Cys Val Ala
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Peptide variant

<400> SEQUENCE: 34

Pro Thr Val Phe Glu Asn Cys Val Ala Asp
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Peptide variant
```

```
<400> SEQUENCE: 35

Thr Val Phe Glu Asn Cys Val Ala Asp Ile
1               5                   10
```